(12) United States Patent
Olsen et al.

(10) Patent No.: US 9,309,414 B2
(45) Date of Patent: Apr. 12, 2016

(54) ENZYME-BASED SELF-POLISHING COATING COMPOSITIONS

(75) Inventors: Stefan Moller Olsen, Copenhagen Ø (DE); Soren Kiil, Holte (DK); Kim Dam-Johansen, Frederiksværk (DK); Lars Thorslund Pedersen, Kgs. Lyngby (DK)

(73) Assignees: HEMPEL A/S, Lyngby (DK); DUPONT NUTRITION BIOSCIENCES APS, Copenhagen K (DK)

( * ) Notice: Subject to any disclaimer, the term of this patent is extended or adjusted under 35 U.S.C. 154(b) by 1188 days.

(21) Appl. No.: 13/148,042

(22) PCT Filed: Feb. 5, 2010

(86) PCT No.: PCT/EP2010/051437
§ 371 (c)(1),
(2), (4) Date: Oct. 19, 2011

(87) PCT Pub. No.: WO2010/089378
PCT Pub. Date: Aug. 12, 2010

(65) Prior Publication Data
US 2012/0031300 A1   Feb. 9, 2012

(30) Foreign Application Priority Data
Feb. 6, 2009   (EP) .................................... 09152264

(51) Int. Cl.
*C12N 11/10* (2006.01)
*C09D 5/16* (2006.01)

(52) U.S. Cl.
CPC ............ *C09D 5/1687* (2013.01); *C09D 5/1606* (2013.01); *C12N 11/10* (2013.01)

(58) Field of Classification Search
None
See application file for complete search history.

(56) References Cited

U.S. PATENT DOCUMENTS

| | | |
|---|---|---|
| 3,607,821 A | 9/1971 | Clarke et al. |
| 4,147,688 A | 4/1979 | Makhlouf et al. |
| 4,493,914 A | 1/1985 | Chattha |
| 4,960,828 A | 10/1990 | Higuchi et al. |
| 5,770,188 A | 6/1998 | Hamade et al. |
| 2002/0106361 A1 | 8/2002 | Poulsen et al. |

FOREIGN PATENT DOCUMENTS

| | | |
|---|---|---|
| EP | 0204456 | 12/1986 |
| EP | 0297505 | 1/1989 |
| EP | 0342276 | 11/1989 |
| EP | 0471204 | 2/1992 |
| EP | 0779304 | 6/1997 |
| EP | 0832245 | 4/1998 |
| EP | 0866103 | 9/1998 |
| JP | 02227465 | 9/1990 |
| JP | 2002-345460 A | 12/2002 |
| WO | WO-96/40935 | 12/1996 |
| WO | WO-97/00919 | 1/1997 |
| WO | WO-97/44401 | 11/1997 |
| WO | WO-00/77102 A1 | 12/2000 |
| WO | WO-2006/002630 | 1/2006 |

OTHER PUBLICATIONS

Olsen et al., Biofouling, 2007, vol. 23, No. 5/6, p. 369-383.*
Yebra, Diego Meseguer et al., "Dissolution rate measurements of sea water soluble pigments for antifouling paints: ZnO," Progress in Organic Coatings, 2006, vol. 56, No, 4, pp. 327-337.
McCleary, Barry V. et al., "Measurement of amyloglucosidase using P=nitrophenyl βmaltoside as substrate," Biotechnology Techniques, 1991, vol. 5, No. 4, pp. 255-258.
Rand, Thomas et al., "Characterization of the flavin association in hexose oxidase from Chrondrus crispus," FEBS Journal, 2006, vol. 273, pp. 2693-2703.
Kill et al., "Marine biofouling protection: design of controlled release antifounling paints in: Ng et al. (eds.)," Chemical Product Design; Towards a Perspective Through Case Studies, 2006, Part II (7).
Kristensen et al., "Biomimetic silica encapsulation of enzymes for replacement of biocides in antifouling coatings," Green Chemistry (Mar. 2010), vol. 12, No. 3, pp. 387-394.

* cited by examiner

*Primary Examiner* — Kade Ariani
(74) *Attorney, Agent, or Firm* — Birch, Stewart, Kolasch & Birch, LLP

(57) ABSTRACT

The present application discloses an enzyme-based self-polishing coating composition comprising a binder phase in the form of a binder system and a pigment phase, said pigment phase comprising (i) a polysaccharide and (ii) an enzyme capable of facilitating hydrolysis of said polysaccharide, said enzyme being immobilized on a carrier material, e.g. on the polysaccharide. The enzyme may be glucoamylase and the polysaccharide may be starch. A marine structure coated with the coating composition; a method for the preparation of the enzyme-based self-polishing coating composition; the use of the polysaccharide and the enzyme in a coating composition to provide self-polishing of said coating composition; and a method for providing a self-polishing effect of a coating composition are also disclosed.

9 Claims, 1 Drawing Sheet

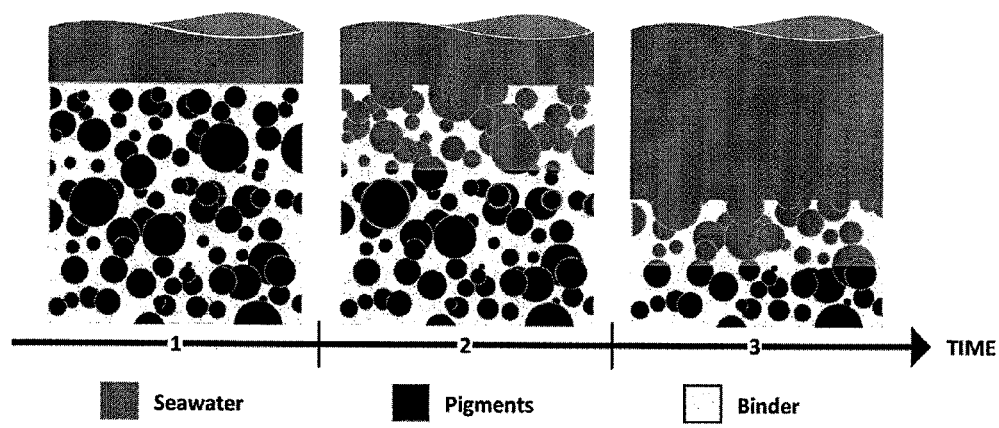

ENZYME-BASED SELF-POLISHING COATING COMPOSITIONS

This application is the National Phase Under 35 U.S.C. §371 of PCT International Application No. PCT/EP2010/051437 which has an International filing date of Feb. 5, 2010, which claims priority to European Patent Application No. 09152264.9 filed on Feb. 6, 2009. The entire contents of all applications listed above are hereby incorporated by reference.

FIELD OF THE INVENTION

The present invention relates to enzyme-based self-polishing coating compositions.

BACKGROUND OF THE INVENTION

In many present self-polishing antifouling coating compositions, copper is a main component in the form of cuprous oxides. Copper is an expensive raw material and the environmental effect of copper is under debate. Consequently, there is a growing interest in antifouling coating compositions with reduced copper content or even products free of copper. One option is to exchange cuprous oxide with zinc oxide (e.g. WO 97/00919), however this approach also have its limitations; e.g. high amounts of zinc oxide may have a negative effect on discoloration. Both cuprous oxide and zinc oxide are slightly soluble in seawater and thereby have a strong effect on the polishing properties of the paint coat (Yebra, D. M., Kiil, S., Weinell, C., Dam-Johansen, K. (2006) Dissolution Rate Measurements of Seawater Soluble Pigments for Antifouling Paints: ZnO. Prog. Org. Coat. 56(4), 327-337). On the other hand, non-soluble materials typically have a negative effect on the polishing properties.

Hence, there is generally a need for self-polishing coating compositions where cuprous oxide and/or zinc oxide is partly or fully replaced with other "pigment/filler" constituents, while maintaining the self-polishing properties.

EP 866103 A1 (Nippon Paint) discloses a method for releasing an antimicrobial compound from a matrix. An enzyme and a substrate for the enzyme are incorporated in the matrix.

U.S. Pat. No. 5,770,188 (Nippon Paint) discloses an antifouling paint composition containing an enzyme-susceptible resin and a lipid-coated enzyme which is stable in organic solvents and is capable of catalysing the degradation of the resin. It is mentioned that an enzyme-susceptible resin may include starch, and that—in such instanced—α-amylase, β-amylase, glucoamylase and the like may be used as the enzyme.

US 2002/01106361 (Danisco) discloses an anti-fouling composition comprising a surface coating material, an enzyme and an enzyme substrate. One enzyme-substrate combination is represented by amyloglucosidase-starch/hexose oxidase-glucose. The composition may be self-polishing.

WO 2006/002630 A1 (Biolocus) discloses a self-polishing anti-fouling coating composition comprising a hydrolysable polymer composition and a first enzyme having anti-fouling activity. In one embodiment, a second enzyme which is capable of hydrolysing the hydrolysable polymer composition is included.

In view of the above, there is a need for alternative self-polishing coating composition.

BRIEF DESCRIPTION OF THE INVENTION

As opposed to some of the earlier described applications of enzymes in antifouling coatings, the invention is directed to the use of enzymes and the corresponding substrates (polysaccharides) in the pigment phase of coating compositions. In order to maintain the enzyme in a functionally intact form and furthermore in close proximity of the polysaccharide, it has been found that the enzyme advantageously is immobilized to a carrier. The carrier is typically another constituent of the pigment phase, and in preferred embodiments the carrier may even be the polysaccharide.

This being said, it has been found that the polysaccharide in combination with a corresponding immobilized enzyme suitably can replace at least a part of the pigments and fillers conventionally used in self-polishing antifouling coating compositions, in particular the water-soluble pigments cuprous oxide and zinc oxide.

FIG. 1 illustrates that seawater-soluble pigments, such as cuprous oxide, are important for obtaining a suitable rate of polishing for antifouling coatings. Dissolution of the seawater-soluble pigments results in a leached layer of porous binder material (residues of the binder phase) filled with seawater. The leached layer dramatically increases the surface-area of the seawater-paint coat interface and thereby accelerates the rate of the reaction leading to dissolution of the residues of the binder phase. A potential substitute for cuprous oxide must therefore also be of a form that allows it to partly or fully constitute the pigment-phase of the coating. In addition to the pigment characteristic, a substitute for cuprous oxide must also be continuously dissolved in the seawater.

The present invention resides on the fact that polysaccharides (in particular in particulate form) are suitable "pigments" for coatings, and enzymes capable of facilitating the hydrolysis thereof can be used to control the dissolution of the polysaccharides. However, generally polysaccharide degrading enzymes are only obtainable in solutions, and formulating a coating with an aqueous solution of enzyme would be troublesome for the production of solvent-based antifouling coatings. Even if pure enzymes are used in the coating production, the enzymes will be susceptible to entrapment in the binder phase of the dry antifouling coating, causing severe loss of enzyme activity. These drawbacks have accordingly been overcome by the present invention by immobilizing the enzymes on a carrier material, in particular a material included in the pigment phase of the antifouling coating composition. In that way, otherwise water-insoluble polysaccharides become applicable as a substitute for e.g. cuprous oxide and zinc oxide in polishing antifouling coatings.

The present inventors have, thus, surprisingly found that incorporation in the pigment phase of a coating composition of a polysaccharide and an enzyme capable of facilitating the hydrolysis of said polysaccharide, and wherein said enzyme is immobilized on a carrier material, provides interesting alternatives to the previously known principles for self-polishing antifouling paint compositions.

Hence, in a first aspect, the invention relates to an enzyme-based self-polishing coating composition comprising a binder phase in the form of a binder system and a pigment phase, said pigment phase comprising (i) a polysaccharide and (ii) an enzyme capable of facilitating hydrolysis of said polysaccharide, said enzyme being immobilized on a carrier material.

In a further aspect, the invention relates to a marine structure coated with one or several successive layers of a coating composition as defined herein. In a still further aspect, the invention relates to a method for the preparation of the enzyme-based self-polishing coating composition as defined herein. In still a further aspect, the invention relates to the use of a polysaccharide and an enzyme capable of facilitating hydrolysis of said polysaccharide, said enzyme being immobilized on a carrier material, in a coating composition to provide self-polishing of said coating composition. In a still further aspect, the invention relates to a method for providing a self-polishing effect of a coating composition, the method comprising the step of incorporating into the coating composition a polysaccharide and an enzyme capable of facilitating hydrolysis of said polysaccharide, said enzyme being immobilized on a carrier material.

BRIEF DESCRIPTION OF THE FIGURES

FIG. 1 shows the mechanisms involved in polishing of an antifouling coating, dividing the process into three steps. 1: An antifouling coating consisting of a binder phase including a binder system and a discontinuous phase including pigments and/or fillers. A freshly immersed antifouling coating will leach seawater-soluble pigments into the sea. 2: Seawater-filled pores left behind by the seawater-soluble pigments constitute the leached layer of the coating. The surface area of the water-paint coat interface is increased by formation of the leached layer, which allows for more interactions between water and the residues of the binder phase. 3: As a result the outermost layer of the paint coat is released into seawater.

DETAILED DESCRIPTION OF THE INVENTION

As mentioned above, the present invention relates to an enzyme-based self-polishing coating composition comprising a binder phase in the form of a binder system and a pigment phase, said pigment phase comprising (i) a polysaccharide and (ii) an enzyme capable of facilitating hydrolysis of said polysaccharide, said enzyme being immobilized on a carrier material.

The Coating Composition

Coating compositions (occasionally referred to as "paints" or "paint compositions") typically consists of a binder phase (which forms the paint film upon drying and thereby corresponds to the continuous phase of the final paint coat) and a pigments phase (corresponding to the discontinuous phase of the final paint coat).

In the present context, the binder phase is in the form of a binder system. Binder systems to be utilized in the present context are conventional systems as will be appreciated by the skilled person. Examples of currently preferred binder systems to be utilised within the concept of the present invention are described further below.

The coating composition also comprises, as a part of the pigment phase, (i) a polysaccharide and (ii) an enzyme capable of facilitating hydrolysis of said polysaccharide. A particular feature of the polysaccharide-enzyme combination is that the enzyme is immobilized on a carrier material. As it will be apparent from the following (see further below), the carrier material may be the polysaccharide for which the enzyme is capable of facilitating hydrolysis, or another polysaccharide (i.e. a polysaccharide for which the enzyme is not capable of facilitating hydrolysis), or a completely different type of carrier material. However, the carrier material is preferably a constituent of the pigment phase.

In most practical embodiments, the binder phase constitutes 30-80% by solids volume of the coating composition and the pigment phase constitutes 20-70% by solids volume of the coating composition. In preferred embodiments, the binder phase constitutes 50-70% by solids volume, such as 55-65% by solids volume of the coating composition and the pigment phase constitutes 30-65% by solids volume, such as 35-55% by solids volume of the coating composition.

When expressed by wet weight, typically the binder phase constitutes 15-70% by wet weight of the coating composition and the pigment phase constitutes 30-85% by wet weight of the coating composition. In preferred embodiments, the binder phase constitutes 20-60% by wet weight of the coating composition and the pigment phase constitutes 40-80% by wet weight of the coating composition.

Without being limited to one particular theory, it is however believed that the combination of the polysaccharide and a corresponding immobilized enzyme (in addition to the effect of any binder phase constituents, pigments, fillers, antifouling agents, etc.) provides a unique possibility for providing a sufficient, even and long-term self-polishing rate.

When used herein, the term "self-polishing" is intended to mean that the paint coat (i.e. the dried film of the coating composition) should have a polishing rate of at least 1 μm per 10,000 Nautical miles (18,520 km), determined in accordance with the "Polishing rate test" specified in the Examples section. Preferably the polishing rate is in the range of 1-50 μm, in particular in the range of 1-30 μm, per 10,000 Nautical miles (18,520 km).

The Pigment Phase
The Polysaccharide

The pigment phase comprises (i) a polysaccharide.

When used herein, the term "polysaccharide" is intended to mean polymers made up of a plurality of monosaccharides joined together by glycosidic bonds. Polysaccharides can be homopolysaccharides (i.e. build-up of essentially the same monosaccharide) or heteropolysaccharides (i.e. build-up of two or more different monosaccharides). Polysaccharides are typically very large, often branched, macromolecules. The molecular weight of suitable polysaccharides is typically at least 5,000 g/mol, in particular at least 500,000 g/mol, such as 1,000,000-100,000,000 g/mol or 5,000,000-20,000,000 g/mol. The polysaccharides in question are preferably water-insoluble as such, or at least comprises 95% by weight of more of water insoluble constituents, but are gradually rendered more water-soluble by interaction with the enzyme(s) and water, when present in the final paint film in accordance with the invention.

Illustrative examples of applicable polysaccharides include starch, glycogen, cellulose (e.g. microcrystalline cellulose), hemicellulose, glycopyranose, amylose, amylopectin, xylan, glucan, pectin, which may be use alone or in a combination of two or more polysaccharides.

The content of water-soluble material in the polysaccharide used should typically not exceed 5% by weight of the polysaccharide.

In one currently preferred embodiment, starch is used as a polysaccharide, in particular as the sole polysaccharide.

Preferably, the starch comprises less than 3% by weight, in particular less than 1% by weight, of waters-soluble constituents.

Also preferably, the starch has a weight average molecular weight of at least 1,000,000 g/mol, such as at least 5,000,000 g/mol e.g. at least 8,000,000 g/mol.

Suitable qualities of starch include "native" starch derived from corn, tapioca, wheat, potato, rice, sago, peas or cycads (see also Example 1).

In another embodiment, cellulose, in particular microcrystalline cellulose, is used as a polysaccharide, in particular as the sole polysaccharide.

The polysaccharide is preferably in particulate form allowing it to simulate the function of a pigment or filler in the pigment phase of the final paint coat. In some preferred embodiments, the average equivalent sphere volume diameter (see, e.g., Example 1) is in the range of 0.5-50 µm, such as 1-25 µm.

The polysaccharide is typically present in an amount of 1-50% by solids volume, such as 1-30% by solids volume, of the coating composition, e.g. 1-10% by solids volume, or 20-30% by solids volume.

In some embodiments, the polysaccharide is present in an amount of 1-70% by solids volume, such as 1-40% by solids volume, of the pigment phase, e.g. 1-15% by solids volume, or 25-40% by solids volume.

When expressed by wet weight, the polysaccharide is typically present in an amount of 1-30 by wet weight, such as 1-20% by wet weight, of the coating composition, e.g. 1-10% by wet weight, or 15-30% by wet weight.

In some embodiments (when expressed by wet weight), the polysaccharide is present in an amount of 1-60% by wet weight, such as 1-35% by wet weight, of the pigment phase, e.g. 1-15% by wet weight, or 20-35% by wet weight.

The Enzyme

The pigment phase further comprises an enzyme which is capable of facilitating hydrolysis of said polysaccharide.

If more than one polysaccharide is present in the pigment phase, the enzyme is capable of facilitating hydrolysis of at least one of said polysaccharides. In one preferred variant of the embodiment where more than one polysaccharide is present, corresponding enzymes capable of facilitating hydrolysis of these polysaccharides are present in the pigment phase.

The expression "capable of facilitating hydrolysis" is intended to mean that the enzyme (or enzymes)—upon expressing its enzymatic action—allows for breaking up glycosidic bonds within the polysaccharide. Upon the enzymatic action, the polysaccharide is broken down into mono- or di- or oligosaccharide fragments. In some interesting embodiments, the enzyme is only capable of facilitating hydrolysis (degradation) of the polysaccharide (e.g. starch) into the corresponding di- or oligosaccharides; hence the enzyme is essentially incapable of facilitating hydrolysis (degradation) of the polysaccharide into the corresponding monosaccharides.

The enzymes are typically selected from glycosidases, i.e. enzymes hydrolysing O- and S-glycosyl compounds (EC 3.2.1.). Amylases, such as α-amylase, β-amylase, glucoamylase and γ-amylase are typically applied.

The selection of the enzyme(s) is—as will be apparent for the skilled person—dependent on the included polysaccharide(s).

In the preferred embodiment, wherein starch is included in the pigment phase, the enzyme is preferably selected from amylases, such as α-amylase, β-amylase, glucoamylase and γ-amylase.

In the embodiment, wherein cellulose, e.g. microcrystalline cellulose, is included in the pigment phase, the enzyme is preferably selected from cellulases, such as endo-1,4-β-glucanase, cellobiohydrolase, β-glucosidase, and glucohydrolase.

The enzymes (e.g. enzyme(s) capable of facilitating hydrolysis of polysaccharides) may be purified enzymes or crude enzymes, and the source of the enzyme(s) includes microorganisms, plants and animals.

In one currently preferred variant, the pigment phase does not include enzymes capable of oxidizing any monosaccharides resulting from the hydrolysis of the polysaccharide. Oxidative species may damage the polysaccharide-degrading enzymes irreversibly.

This being said, the enzyme is typically present in such an amount that the ratio between said enzyme and said polysaccharide is 0.05-200,000 milliunits enzyme(s) per g polysaccharide e.g. 10-200,000 milliunits enzyme(s) per g polysaccharide, such as 10-75,000 milliunits enzyme(s) per g polysaccharide, more preferably 0.5-20,000 milliunits enzyme(s) per g polysaccharide, such as 50-20,000 milliunits enzyme(s) per g polysaccharide, more preferably 0.1-10,000 milliunits enzyme(s) per g polysaccharide, such as 100-10,000 milliunits enzyme(s) per g polysaccharide.

The activity of the enzyme glucoamylase is determined according to the method described in McCleary et al. (1991) Biotechnology Techniques, 5, 255-258. An activity of 1 U (one unit) corresponds to the amount of glucoamylase releasing 1 µmol glucose per minute at 40° C. and pH 4.5 using the synthetic soluble p-nitrophenyl β-maltoside substrate. It should be understood, that the activity of the enzyme is determined prior to immobilisation of the enzyme to the carrier.

For other enzymes, an activity of 1 U (one unit) generally corresponds to the amount of enzyme releasing 1 µmol monosaccharide units per minute. The activity is typically measured at a temperature of 40° C. and a pH of 4.5.

In a preferred embodiment comprising starch, the enzyme is present in such an amount that the ratio between said enzyme and said starch is 0.05-200,000 milliunits enzyme(s) per g starch e.g. 10-200,000 milliunits enzyme(s) per g starch, such as 10-75,000 milliunits enzyme(s) per g starch, more preferably 0.5-20,000 milliunits enzyme(s) per g starch, such as 50-20,000 milliunits enzyme(s) per g starch, more preferably 0.1-10,000 milliunits enzyme(s) per g starch, such as 100-10,000 milliunits enzyme(s) per g starch.

Carrier for Polysaccharide Degrading Enzyme

The enzyme(s) is/are immobilized on a carrier.

Immobilisation may either be via covalent bonds or by non-covalent bonding, e.g. affinity binding, hydrogen bonding, ionic bonding, etc., between the enzyme and the carrier. In certain cases, the enzyme (e.g. an amylase when the polysaccharide is starch) may include a site specifically adapted for binding to the polysaccharide (the substrate), and hence the polysaccharide may be a suitable carrier. These latter variants are—contrary to what should have been believed—found to be particularly interesting, although enzymes are not commonly formulated on their substrates because the enzyme-facilitated hydrolysis may occur at a premature stage.

In a currently preferred embodiment, immobilisation is via non-covalent bonding.

In a currently preferred embodiment of the invention, the enzyme is immobilised on the polysaccharide (in particular its corresponding substrate). Hence, in the variant where the polysaccharide is starch, the enzyme (preferably an amylase) is immobilized on the starch. In the variant where the polysaccharide is cellulose, e.g. microcrystalline cellulose, the enzyme (preferably a cellulase) is immobilized on the cellulose.

In another embodiment, the enzyme is immobilised on a carrier materials not being a polysaccharide hydrolysis of which the enzyme is capable of facilitating. Within this embodiment, the carrier material is preferably selected from a list of materials commonly present in the pigment phase of antifouling coatings. The materials may, e.g., be selected from polysaccharides (i.e. non-substrates for the enzyme), oligosaccharides, sugars, silicates, such as silica (e.g. fumed silica), metal oxides such as titanium dioxide, alumina, ferrous oxide and ferric oxide, and graphite.

Immobilising the enzymes on a carrier material gives rise to additional material in the coating composition, which may affect the coating performance negatively. Therefore, the substrates of the enzymes are preferred as carrier material in some embodiments. However, using the enzymes own substrates as carrier induces the potential of degradation of the polysaccharide before the material has been enclosed in a coating, and therefore it may in other embodiments be preferred to use a pigment and filler materials commonly applied in antifouling coating production as a carrier for the enzymes.

Hydrolytic enzymes are preferred because they require water before the reaction takes place. They can therefore be immobilised on their own substrates without reactions occurring, as long as water activity is limited, or the enzyme activity is controlled by other means (pH, temperature, salinity, inhibitors) until there is no water left in the material.

Other Constituents of the Pigment Phase

The pigment phase (i.e. the phase corresponding to the discontinuous phase of the final (dry) paint coat) may of course also include pigments, filler, fibres, and antifouling agents, as well as other suitable constituents to be included in the pigment phase of coating compositions.

Such other constituents of the pigment phase (i.e. constituents besides the polysaccharide(s), the enzyme(s) and any carriers) are not strictly mandatory components. However, such other constituents are typically incorporated in a total amount of up to 60%, such as up to 50% by solids volume, e.g. in amounts of 20-50% or 35-50% by solids volume of the coating composition. When related to the wet weight of the total composition, such other constituents are typically incorporated in a total amount of up to 60%, such as up to 50% by wet weight, e.g. in amounts of 0.1-40%, or 0.1-30%, by wet weight of the coating composition.

Examples of pigments are grades of metal oxides such as cuprous oxide ($Cu_2O$) and cupric oxide (CuO) (even though e.g. cuprous oxide and cupric oxide may have antifouling agent characteristics, it is understood that in the present context such metal oxides are only considered as "pigments"), titanium dioxide, red iron oxide, zinc oxide, carbon black, graphite, yellow iron oxide, red molybdate, yellow molybdate, zinc sulfide, antimony oxide, sodium aluminium sulfosilicates, quinacridones, phthalocyanine blue, phthalocyanine green, titaniurndioxide, black iron oxide, graphite, indanthrone blue, cobalt aluminium oxide, carbazole dioxazine, chromium oxide, isoindoline orange, bis-acetoacet-o-tolidiole, benz-imidazolon, quinaphtalone yellow, isoindoline yellow, tetrachloroisoindolinone, quinophthalone yellow. Such materials are characterised in that they render the final paint coat non-transparent and non-translucent.

When cuprous oxide is present in the coating composition, the $Cu_2O$ content is preferably 1-40% by solids volume, such as in the range of 5-35% by solids volume of the coating composition. When expressed by wet weight of the coating composition, and when cuprous oxide is present, the $Cu_2O$ content is preferably at least 5% by wet weight, such as in the range of 10-75% by wet weight of the coating composition.

The pigments phase may further include pigment-like ingredients such as fillers.

Examples of fillers are calcium carbonate, dolomite, talc, mica, barium sulfate, kaolin, silica (including pyrogenic silica, colloidal silica, fumed silica, etc.), perlite, magnesium oxide, calcite and quartz flour, molecular sieves, synthetic zeolites, calcium silicophosphate, hydrated aluminium silicate (bentonite), organo-midified clays, anhydrous gypsum, etc.

These materials are characterised in that they do not render the final paint coat non-translucent and therefore do not contribute significantly to hide any material below the final paint coat.

It should be noted that some of the fillers (and pigments) may provide certain advantageous properties of the types provided by the additives of the binder phase (e.g. as stabilizers against moisture, dehydrating agents, water scavengers, thickeners and anti-settling agents, etc.), however for the purpose of the present application with claims, such particulate materials are to be construed as being part of the pigment phase.

Examples of fibres are e.g. those generally and specifically described in WO 00/77102, which is hereby incorporated by reference.

In order for a certain particle to be considered as a fibre within the present context, the ratio between the greatest dimension and the smallest dimension perpendicular to the length dimension in substantially all points along the longitudinal axis (the length dimension–longest dimension) should not exceed 2.5:1, preferably not exceeding 2:1. Furthermore, the ratio between the longest dimension and the average of the two shortest dimensions should be at least 5:1. Thus, fibres are characterised of having one long dimension and two short dimension, where the long dimension is substantially longer than the two short dimensions (typically by an order of magnitude, or even more), and the two short dimensions are substantially equal (of the same order of magnitude). For completely regular fibres, i.e. fibres having a cylindrical shape, it is evident how to determine the "length" (longest dimension) and the two (identical) shortest dimensions. For more irregular fibres, it is believed that the relationship between the dimensions can be evaluated by the following hypothetical experiment: A regular, right-angled box is constructed around the fibre. The box is constructed so as to have the smallest possible volume, as it should fully comprise the fibre. To the extent that the fibre is curved, it is (again hypothetically) assumed that the fibre is flexible so that the volume of the hypothetical box can be minimised by "bending" the fibre. In order for the "fibre" to be recognised as such in the present context, the ratio between the two smallest dimensions of the box should be at the most 2.5:1 (preferably 2:1) and the ratio between the longest dimension of the box and the average of the to smallest dimensions of the box should be at least 5:1.

At present, especially preferred are mineral fibres such as mineral-glass fibres, wollastonite fibres, montmorillonite fibres, tobermorite fibres, atapulgite fibres, calcined bauxite fibres, volcanic rock fibres, bauxite fibres, rockwool fibres, and processed mineral fibres from mineral wool.

When present, the concentration of the fibres is normally in the range of 0.5-15%, e.g. 1-10% by solids volume of the coating composition.

When related to the total composition (wet weight), and when present, the concentration of the fibres is normally in the range of 0.1-20%, e.g. 0.5-10%, by wet weight of the coating composition.

It should be understood that the above ranges refer to the total amount of fibres, thus, in the case where two or more fibre types are utilised, the combined amounts should fall within the above ranges.

The coating composition may also comprise one or more antifouling agents as is customary within the field. Examples of antifouling agents are: metallo-dithiocarbamates such as bis(dimethyldithiocarbamato)zinc, ethylene-bis(dithiocarbamato)zinc, ethylene-bis(dithiocarbamato)manganese, and complexes between these; bis(1-hydroxy-2(1H)-pyridinethionato-O,S)-copper; copper acrylate; bis(1-hydroxy-2(1H)-pyridinethionato-O,S)-zinc; phenyl(bispyridyl)-bismuth dichloride; metal biocides such as copper, copper metal alloys such as copper-nickel alloys; metal salts such as cuprous thiocyanate, basic copper carbonate, copper hydroxide, barium metaborate, and copper sulphide; heterocyclic nitrogen compounds such as 3a,4,7,7a-tetrahydro-2-((trichloromethyl)-thio)-1H-isoindole-1,3(2H)-dione, pyridine-triphenylborane, 1-(2,4,6-trichlorophenyl)-1H-pyrrole-2,5-dione, 2,3,5,6-tetrachloro-4-(methylsulfonyl)-pyridine, 2-methylthio-4-tert-butylamino-6-cyclopropylamines-triazin, and quinoline derivatives; heterocyclic sulfur compounds such as 2-(4-thiazolyl)-benzimidazole, 4,5-dichloro-2-n-octyl-4-isothiazolin-3-one, 4,5-dichloro-2-octyl-3(21-1)-isothiazoline, 1,2-benzisothiazolin-3-one, and 2-(thiocyanatomethylthio)-benzothiazole; urea derivatives such as N-(1,3-bis(hydroxymethyl)-2,5-dioxo-4-imidazolidinyl)-N,N'-bis(hydroxymethyl)urea, and N-(3,4-dichlorophenyl)-N,N-dimethylurea, N,N-dimethyl-chlorophenylurea; amides or Imides of carboxylic acids; sulfonic acids and of sulfenic acids such as 2,4,6-trichlorophenyl maleimide, 1,1-dichloro-N-((dimethylamino)sulfonyl)-1-fluoro-N-(4-methylphenyl)-methanesulfenamide, 2,2-dibromo-3-nitrilo-propionamide, N-(fluorodichloromethylthio)-phthalimide, N,N-dimethyl-N'-phenyl-N'-(fluorodichloromethylthio)-sulfamide, and N-methylol formamide; salts or esters of carboxylic acids such as 2-((3-iodo-2-propynyl)oxy)-ethanol phenylcarbamate and N,N-didecyl-N-methyl-poly(oxyethyl)-ammonium propionate; amines such as dehydroabiethylamines and cocodimethylamine; substituted methane such as di(2-hydroxy-ethoxy)methane, 5,5'-dichloro-2,2'-dihydroxy-diphenylmethane, and methylene-bisthiocyanate; substituted benzene such as 2,4,5,6-tetrachloro-1,3-benzenedicarbonitrile, 1,1-dichloro-N-((dimethylamino)-sulfonyl)-1-fluoro-N-phenylmethanesulfenamide, and 1-((diiodomethyl)sulfonyl)-4-methyl-benzene; tetraalkyl phosphonium halogenides such as tri-n-butyltetradecyl phosphonium chloride; guanidine derivatives such as n-dodecylguanidine hydrochloride; disulfides such as bis-(dimethylthiocarbamoyl)-disulfide, tetramethylthiuram disulfide; imidazole containing compound, such as medetomidine; 2-(p-chlorophenyl)-3-cyano-4-bromo-5-trifluoromethyl pyrrole and mixtures thereof.

Presently, it is preferred that the antifouling agent is an agent that does not comprise tin.

In one preferred embodiment the coating composition comprises an antifouling agent selected from the group consisting of pyridine-triphenylborane, 2-(p-chlorophenyl)-3-cyano-4-bromo-5-trifluoromethyl pyrrole and imidazole containing compounds, such as medetomidine.

The total amount of the antifouling agent(s), if present, is typically in the range of up to 30%, such as 0.05-25%, by solids volume of the coating composition, e.g. 0.05-20% by solids volume of the coating composition.

When related to the total weight of the coating composition, the total amount of the antifouling agent(s), if present, is typically in the range of 0-40%, such as 0.05-30%, by wet weight of the coating composition, e.g. 0.05-20% by wet weight of the coating composition.

The Binder Phase

The binder phase of the coating composition forms the paint film upon drying and thereby corresponds to the continuous phase of the final (dry) paint coat.

Virtually all binder systems conventionally used in self-polishing coating compositions may be used as the binder phase of the present coating composition. It is also found that with respect to the relative amounts of binder system vs. pigments/fillers/etc., only minor modifications (optimizations) may be necessary in order to obtain suitable polishing rates.

For the purpose of illustrating the scope of the present invention with respect to possible types of binder systems, a number of examples of binder systems for marine purposes and yacht purposes, respectively, are provided in the following.

For yacht purposes it is believed that, the following types of constituents within the binder system are especially interesting; (natural) rosin, rosin derivatives, disproportionated rosin, partly polymerised rosin, hydrogenated rosin, gum rosin, disproportionated gum rosin, acrylic resins, polyvinyl methyl ether, and vinyl acetate-vinylchloride-ethylene terpolymers. Such constituent may also be present in binder systems for marine purposes.

For marine purposes, it is believed that non-aqueous dispersion binder systems, silylated acrylate binder systems and metal acrylate binder system are especially interesting. These binder systems will—for illustrative purposes—be describe in further detail in the following.

Non-Aqueous Dispersion Binder System

The terms "non-aqueous dispersion resin", "NAD" and similar expressions are intended to mean a shell-core structure that includes a resin obtained by stably dispersing a high-polarity, high-molecular weight resin particulate component (the "core component") into a non-aqueous liquid medium in a low-polarity solvent using a high-molecular weight component (the "shell component").

The non-aqueous dispersion resin may be prepared by a method wherein a polymerisable ethylenically unsaturated monomer which is soluble in a hydrocarbon solvent and which is polymerisable to form a polymer (the core component) which is insoluble in the hydrocarbon solvent, is subjected to dispersion polymerisation in accordance with a conventional method in the hydrocarbon solvent in the presence of a shell component (the dispersion stabiliser) made of a polymer which dissolves or swells in the solvent.

The non-aqueous dispersion-type resin utilised in this invention can be a resin known per se; or it can be produced like the known resins. Such non-aqueous dispersion-type resins and method for their preparation are described in, e.g., U.S. Pat. No. 3,607,821, U.S. Pat. No. 4,147,688, U.S. Pat. No. 4,493,914 and U.S. Pat. No. 4,960,828, Japanese Patent Publication No. 29,551/1973 and Japanese Laid-open Patent Application No. 177,068/1982. Specifically, as the shell component constituting the non-aqueous dispersion-type resin, various high-molecular substances soluble in a low-polarity solvent which are described in, e.g., U.S. Pat. No. 4,960,828 (Japanese Laid-open Patent Application No. 43374/1989), can be used.

From the aspect of antifouling property of the final paint coat, shell components such as an acrylic resin or a vinyl resin may be used.

As the core component, a copolymer of an ethylenically unsaturated monomer having a high polarity is generally applicable.

Preferably the core component of the non-aqueous dispersion-type resin has free acid groups or silyl ester groups that are convertible into the acid group by hydrolysis in sea water or combinations thereof. Preferably 5-75% by weight, e.g. 5-60% by weight or 7-50% by weight, of the monomers of the core polymer should carry free acid groups or silyl ester groups or combinations thereof. As the free acid groups will have direct influence on the properties of the paint formulation, whereas the silyl ester groups will only have influence after hydrolysis in seawater, it is presently preferred to have an overweight of free acid groups.

Examples of silyl ester monomers are silyl esters of acrylic or methacrylic acid.

If desired, a smaller proportion of the free acid groups or silyl ester groups may also be contained in the shell component.

The expression "free acid group" is intended to cover the acid group in the acid form. It should be understood that such acid groups temporarily may exist on salt form if a suitable counter ion is present in the composition or in the environment. As an illustrative example, it is envisaged that some free acid groups may be present in the sodium salt form if such groups are exposed to salt water.

Preferably the non-aqueous dispersion-type resin has a resin acid value of usually 15-400 mg KOH/g, preferably 15 to 300 mg KOH/g, such as 18 to 300 mg KOH/g. If the total acid value of the NAD resin is below 15 mg KOH/g, the polishing rate of the paint coat is too low and the antifouling property will often be unsatisfactory. On the other hand, if the total acid value is above 400 mg KOH/g, the polishing rate is too high for that reason a problem of water resistance (durability of the paint coat in seawater) becomes a problem. (When the core component and/or the shell component contain the acid precursor group, the resin acid value is one given after the group is converted into the acid group by hydrolysis), The "resin acid value" here referred to is an amount (mg) of KOH consumed to neutralise 1 g of a resin (solids content), expressing a content of an acid group (in case of the acid precursor group, a content of an acid group formed by hydrolysis) of the resin (solids content).

It is advisable that the acid group and/or the acid precursor group is contained in the core component such that the content thereof is, as a resin acid value, at least 80%, preferably at least 90%, more preferably at least 95% of the total resin acid value of the non-aqueous dispersion-type resin.

This being said, it is normally preferred that the shell component is hydrophobic.

The dry weight ratio of the core component to the shell component in the NAD resin is not especially limited, but is normally in the range of 90/10 to 10/90, preferably 80/20 to 25/75, such as 60/40 to 25/75.

Silylated Acrylate Binder System

In one interesting embodiment of the invention the binder system to be used in the coating composition according to the invention comprises a silylated acrylate co-polymer having at least one side chain bearing at least one terminal group of the general formula I:

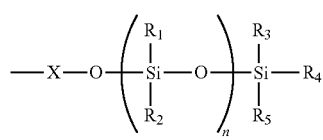

(I)

wherein n is an integer of 1 or more and X, $R_1$, $R_2$, $R_3$, $R_4$ and $R_5$ are as defined above.

While n is an integer of 1, 2, 3, 4 or more, it is in these cases preferred that n is up to about 5,000, such as 1-50 such as 2-15. $R_1$-$R_5$ are each groups selected from the group consisting of $C_{1-20}$-alkyl, $C_{1-20}$-alkoxy, phenyl, optionally substituted phenyl, phenoxy and optionally substituted phenoxy. With respect to the above formula I it is generally preferred that each of the alkyl and alkoxy groups has up to about 5 carbon atoms ($C_{1-5}$-alkyl). Illustrative examples of substituents for the substituted phenyl and phenoxy groups include halogen, $C_{1-5}$-alkyl, $C_{1-5}$-alkoxy or $C_{1-10}$-alkylcarbonyl. As indicated above, $R_1$-$R_5$ may be the same or different groups.

Monomers comprising the terminal groups of the general formula I above may be synthesised as described in EP 0 297 505 B1.

Such monomers may be co-polymerised (in order to obtain the co-polymer with a vinyl polymerisable monomer A. Examples of suitable vinyl polymerisable monomers Include methacrylate esters such as methyl methacrylate, ethyl methacrylate, butyl methacrylate, 2-ethylhexyl methacrylate, 2-hydroxyethyl methacrylate and methoxy ethyl methacrylate; acrylate esters such as ethyl acrylate, butyl acrylate, 2 ethylhexyl acrylate and 2-hydroxyethyl acrylate; maleic acid esters such as dimethyl maleate and diethyl maleate; fumaric acid esters such as dimethyl fumarate and diethyl fumarate; styrene, vinyltoluene, α-methylstyrene, vinyl chloride, vinyl acetate, butadiene, acrylamide, acrylonitrile, methacrylic acid, acrylic acid, isobornyl methacrylate and maleic acid.

The amount of vinyl polymerisable monomers is not more than 95% by weight of the total weight of the resulting co-polymer, preferably not more than 90% by weight. Accordingly, the amount of monomers comprising the terminal groups of the general formula I above is at feast 5% by weight, in particular at least 10% by weight.

The co-polymers preferably have weight average molecular weights in the range of 1,000-1,500,000, such as in the range of 5,000-1,500,000, e.g. in the range of 5,000-1,000,000, in the range of 5,000-500,000, in the range of 5,000-250,000, or in the range of 5,000-100,000. In another interesting embodiment of the invention the binder system to be used in the coating composition according to the invention comprises a silylated acrylate copolymer having at feast one side chain bearing at least one terminal group of the general formula II:

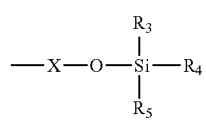

(II)

wherein X, $R_3$, $R_4$ and $R_5$ are as defined above.

Examples of monomers having a terminal group of the general formula II (shown above) are acid functional vinyl polymerisable monomers, such as monomers derived from acrylic acid, methacylic acid, maleic acid (preferably in the form of a monoalkyl ester with 1-6 carbon atoms) or fumaric acid (preferably in the form of a monoalkyl ester with 1-6 carbon atoms).

With respect to the triorganosilyl group, i.e. the —Si($R_3$)($R_4$)($R_5$) group, shown in the above formulae I or II, $R_3$, $R_4$ and $R_5$ may be the same or different, such as $C_{1-20}$-alkyl (e.g. methyl, ethyl, propyl, butyl, cycloalkyl such as cyclohexyl and substituted cyclohexyl); aryl (e.g., phenyl and naphthyl) or substituted aryl (e.g., substituted phenyl and substituted naphthyl). Examples of substituents for aryl halogen, $C_{1-18}$-alkyl, $C_{1-10}$-acyl, sulphonyl, nitro, or amino.

Thus, specific examples of a suitable triorganosilyl group (i.e. the —Si($R_3$)($R_4$)($R_5$) group) shown in the general formula I or II include trimethylsilyl, triethylsilyl, tri-n-propylsilyl, tri-n-butylsilyl, tri-/so-propylsilyl, tri-n-pentylsilyl, tri-n-hexylsilyl, tri-n-octylsilyl, tri-n-dodecylsilyl, triphenylsilyl, tri-p-methylphenylsilyl, tribenzylsilyl, tri-2-methylisopropylsilyl, tri-tert-butyl-silyl, ethyldimethylsilyl, n-butyldimethylsilyl, di-iso-propyl-n-butylsilyl, n-octyl-di-n-butylsilyl, di-iso-propryloctadecylsilyl, dicyclohexylphenylsilyl, tert-butyldiphenylsilyl, dodecyldiphenylsilyl and diphenylmethylsilyl.

Specific examples of suitable methacrylic acid-derived monomers bearing at least one terminal group of the general formula I or II include trimethylsilyl (meth)acrylate, triethylsilyl(meth)acrylate, tri-n-propylsilyl(meth)acrylate, triisopropylsilyl (meth)acrylate, tri-n-butylsilyl (meth)acrylate, triisobutylsilyl (meth)acrylate, tri-tert-butylsilyl(meth)acrylate, tri-n-amylsilyl(meth)acrylate, tri-n-hexylsifyl (meth)acrylate, tri-n-octylsifyl (meth)acrylate, tri-n-dodecylsifyl (meth)acrylate, triphenylsilyl (meth)acrylate, tri-p-methylphenylsilyl (meth)acrylate, tribenzylsilyl (meth)acrylate, ethyldimethylsilyl (meth)acrylate, n-butyldimethylsilyl (meth)acrylate, diisopropyl-n-butylsilyl (meth)acrylate, n-octyldi-n-butylsilyl (meth)acrylate, diisopropylstearylsilyl (meth)acrylate, dicyclohexylphenylsilyl (meth)acrylate, t-butyldiphenyl-silyl(meth)acrylate, and lauryldiphenylsifyl (meth)acrylate.

Specific examples of suitable maleic acid-derived and fumaric acid-derived monomers bearing at least one terminal group of the general formula I or II include triisopropylsilyl methyl maleate, triisopropylsilyl amyl maleate, tri-n-butylsilyl n-butyl maleate, tert-butyldiphenylsilyl methyl maleate, t-butyldiphenylsilyl n-butyl maleate, triisopropylsilyl methyl fumarate, triisopropylsilyl amyl fumarate, tri-n-butylsilyl n-butyl fumarate, tert-butyldiphenylsilyl methyl fumarate, and tert-butyldiphenylsilyl n-butyl fumarate.

In an interesting embodiment of the present invention, the co-polymer to be used in the binder system comprises monomer units with a terminal group of the general formula II (as discussed above) in combination with a second monomer B of the general formula III:

$$Y\text{---}(CH(R_A)\text{---}CH(R_B)\text{---}O)_p\text{---}Z \qquad (III)$$

wherein Z is a $C_{1-20}$-alkyl group or an aryl group; Y is an acryloyloxy group, a methacryloyloxy group, a maleinoyloxy group or a fumaroyloxy group; $R_A$ and $R_B$ are independently selected from the group consisting of hydrogen, $C_{1-20}$-alkyl and aryl; and p is an integer of 1 to 25.

If p>2, $R_A$ and $R_B$ are preferably hydrogen or $CH_3$, i.e. if p>2 the monomer B is preferably derived from a polyethylene glycol or a polypropylene glycol.

If p=1 it is contemplated that monomers, wherein $R_A$ and $R_B$ are larger groups, such as $C_{1-20}$-alkyl or aryl, may also be useful for the purposes described herein.

As shown in formula III, monomer B has in its molecule an acryloyloxy group, a methacryloyloxy group, a maleinoyloxy group (preferably in the form of a mono-$C_{1-6}$-alkyl ester), or a fumaroyloxy group (preferably in the form of a mono-$C_{1-6}$-alkyl ester) as an unsaturated group (Y) and also alkoxy- or aryloxypolyethylene glycol. In the alkoxy- or aryloxypolyethylene glycol group, the degree of polymerisation (p) of the polyethylene glycol is from 1 to 25.

Specific examples of monomer B which has a (meth)acryloyloxy group in a molecule include methoxyethyl (meth)acrylate, ethoxyethyl (meth)acrylate, propoxyethyl (meth)acrylate, butoxyethyl (meth)acrylate, hexoxyethyl (meth)acrylate, methoxydiethylene glycol (meth)acrylate, methoxytriethylene glycol (meth)acrylate, ethoxydiethylene glycol (meth)acrylate, and ethoxytriethylene glycol (meth)acrylate.

Specific examples of monomer B which has a maleinoyloxy or fumaroyloxy group in a molecule include methoxyethyl n-butyl maleate, ethoxydiethylene glycol methyl maleate, ethoxytriethylene glycol methyl maleate, propoxydiethylene glycol methyl maleate, butoxyethyl methyl maleate, hexoxyethyl methyl maleate, methoxyethyl n-butyl fumarate, ethoxydiethylene glycol methyl fumarate, ethoxytriethylene glycol methyl fumarate, propoxydiethylene glycol methyl fumarate, butoxyethyl methyl fumarate, and hexoxyethyl methyl fumarate.

As will be understood by the person skilled in the art, other vinyl monomers may be incorporated in the resulting co-polymer comprising either monomer units having a terminal group of the general formula II (shown above) or in the resulting co-polymer comprising monomer units having a terminal group of the general formula II (shown above) in combination with the second monomer B of the formula III (shown above).

With respect to other monomers co-polymerisable with the above-mentioned monomers, use may be made of various vinyl monomers such as the vinyl polymerisable monomers (A) discussed above.

It is preferred that the proportion of the monomer having a terminal group of the general formula II is from 1-95% by weight, that of monomer B is from 1-95% by weight, and that of other monomer(s) co-polymerisable therewith is from 0-95% by weight on the basis of the total weight of the monomers.

The molecular weight of the resulting co-polymer thus obtained is desirably in the range of 1,000-150,000, such as in the range of 3,000-100,000, e.g. in the range of 5,000-100,000 in terms of weight-average molecular weight. In a further interesting embodiment of the present invention, the binder system to be used in the coating composition according to the invention comprises a co-polymer having monomer units with a terminal group of the general formula II (as discussed above) in combination with a second monomer C of the general formula IV:

(IV)

wherein Y is an acryloyloxy group, a methacryloyloxy group, a maleinoyloxy group or a fumaroyloxy group, and both of $R_6$ and $R_7$ are $C_{1-12}$-alkyl.

As shown in formula IV, monomer C has in its molecule an acryloyloxy group, a methacryloyloxy group, a maleinoyloxy group (preferably in the form of a mono-$C_{1-6}$-alkyl ester), or a fumaroyloxy group (preferably in the form of a mono-$C_{1-6}$alkyl ester) as an unsaturated group (Y) and also a hemiacetal group.

Monomer C can be prepared by an ordinary addition reaction of a carboxy group-containing vinyl monomer selected from acrylic acid, methacrylic acid, maleic acid (or monoester thereof), and fumaric acid (or monoester thereof), with an alkyl vinyl ether (e.g., ethyl vinyl ether, propyl vinyl ether, butyl vinyl ether, hexyl vinyl ether, and 2-ethylhexyl vinyl ether), or a cycloalkyl vinyl ether (e.g., cyclohexyl vinyl ether).

As will be understood by the person skilled in the art, other vinyl monomers may be incorporated in the resulting co-polymer comprising monomer units having a terminal group of the general formula II (shown above) in combination with the second monomer C of the formula IV (shown above).

With respect to other monomers co-polymerisable with the above-mentioned monomers, use may be made of various vinyl monomers such as the vinyl polymerisable monomers (A) discussed above.

It is preferred that the proportion of the monomer having a terminal group of the general formula II is from 1-95% by weight (preferably from 1-80% by weight), that of monomer C is from 1-95% by weight (preferably from 1-80% by weight), and that of other monomer(s) co-polymerisable therewith is up to 98% by weight on the basis of the total weight of the monomers.

The molecular weight of the co-polymer is desirably in the range of 1,000-150,000, preferably in the range of 3,000-100,000, such as in the range of 5,000-100,000 in terms of weight-average molecular weight.

Metal Acrylate Binder System

In an interesting embodiment of the invention the binder system to be used in the coating composition according to the invention comprises a metal acrylate co-polymer having at least one side chain bearing at least one terminal group of the general formula V:

—X—O-M-(L)$_n$ (V)

wherein X is —C(=O)—, —S(=O)$_2$—, —P(=O)(OH)—; M is a metal having a valency of 2 or more n is an integer of 1 or more with the proviso that n+1 equals the metal valency; L is an organic acid residue and each L is independently selected from the group consisting of

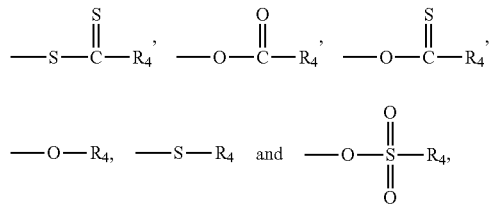

wherein R$_4$ is a monovalent organic residue, or L is —OH or combinations thereof; R$_3$ is hydrogen or a hydrocarbon group having from 1 to 10 carbon atoms.

Examples of monomers having a terminal group of the general formulae V (shown above) are acid-functional vinyl polymerisable monomers, such as methacrylic acid, acrylic acid, p-styrene sulfonic acid, 2-methyl-2-acrylamide propane sulfonic acid, methacryl acid phosphoxy propyl, methacryl 3-chloro-2-acid phosphoxy propyl, methacryl acid phosphoxy ethyl, itaconic acid, maleic acid, maleic anhydride, monoalkyl itaconate (e.g. methyl, ethyl, butyl, 2-ethyl hexyl), monoalkyl maleate (e.g. methyl, ethyl, butyl, 2-ethyl hexyl; half-ester of acid anhydride with hydroxyl containing polymerisable unsaturated monomer (e.g. half-ester of succinic anhydride, maleic anhydride or phthalic anhydride with 2-hydroxy ethyl methacrylate.

The above-mentioned monomers may be co-polymerised (in order to obtain the co-polymer with one or more vinyl polymerisable monomers. Examples of such vinyl polymerisable monomers are methyl acrylate, methyl methacrylate, ethyl acrylate, ethyl methacrylate, propyl acrylate, propyl methacrylate, butyl acrylate, butyl methacrylate, octyl acrylate, octyl methacrylate, 2-ethyl hexyl acrylate, 2-ethyl hexyl methacrylate, methoxy ethyl methacrylate, styrene, vinyl toluene, vinyl pyridine, vinyl pyrolidone, vinyl acetate, acrylonitrile, methacrylonitrile, dimethyl itaconate, dibutyl itaconate, di-2-ethyl hexyl itaconate, dimethyl maleate, di(2-ethyl hexyl) maleate, ethylene, propylene and vinyl chloride.

With respect to the ligand (L), each individual ligand is preferably selected from the group consisting of

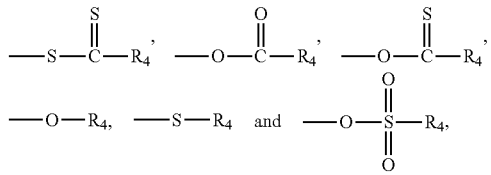

wherein R$_4$ is a monovalent organic residue.
Preferably, R$_4$ is selected from the group consisting of

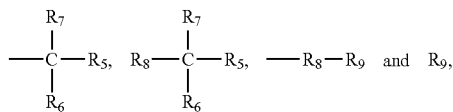

wherein R$_5$ is hydrogen or a hydrocarbon group having from 1 to 20 carbon atoms; R$_6$ and R$_7$ each independently represents a hydrocarbon group having from 1 to 12 carbon atoms; R$_8$ is a hydrocarbon group having from 1 to 4 carbon atoms; and R$_9$ is cyclic hydrocarbon group having from 5 to 20 carbon atoms, such as abietic acid, pallustric acid, neoabietic acid, levopimaric acid, dehydroabietic acid, pimaric acid, isopimaric acid, sandaracopimarlc acid and Δ8,9-isoplmaric acid.

Examples of compounds which may be used as ligands are:
(1) Compounds comprising the group

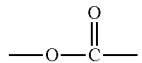

e.g. aliphatic acids, such as levulinic acid; alicyclic acids, such as naphthenic acid, chaulmoogric acid, hydnocarpusic acid, neo abietic acid, levo pimaric acid, palustric acid, 2-methyl-bicyclo-2,2,1-heptane-2-carboxylic acid; aromatic carboxylic acids such as salicylic acid, cresotic acid, α-naphthoic acid, β-naphthoic acid, p-oxy benzoic acid; halogen containing aliphatic acids, such as monochloro acetic acid, monofluoro acetic acid; halogen containing aromatic acids, such as 2,4,5-trichloro phenoxy acetic acid, 2,4-dichloro phenoxy acetic acid, 3,5-dichloro benzoic acid; nitrogen-containing organic acids, such as quinoline carboxylic acid, nitro benzoic acid, dinitro benzoic acid, nitronaphthalene carboxylic acid; lactone carboxylic acids, such as pulvinic acid, vulpinic acid; uracil derivatives, such as uracil-4-carboxylic acid, 5-fluoro uracil-4-carboxylic acid, uracil-5-carboxylic acid; penicillin-derived carboxylic acids, such as penicillin V, ampicillin, penicillin BT, penicillanic acid, penicillin G, penicillin O; Rifamycin B, Lucensomycin, Salcomycin, chloramphenicol, variotin, Trypacidine; and various synthetic fatty acids.

(2) Compounds comprising the group

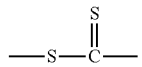

e.g. dimethyl dithiocarbamate and other dithiocarbamates.

(3) Compounds comprising the group

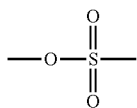

e.g. sulphur containing aromatic compounds, such as 1-naphthol-4-sulphonic acid, p-phenyl benzene sulphonic acid, β-naphthalene sulphonic acid and quinoline sulphonic acid.

(4) Compounds comprising the group

such as compounds comprising the following groups

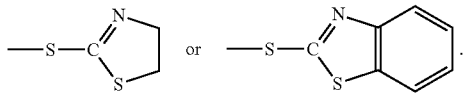

(5) Compounds comprising the group

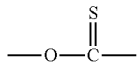

such as various thiocarboxylic compounds.

(6) Compounds comprising the group —O— or —OH e.g. phenol, cresol, xylenol, thymol, carvacol, eugenol, isoeugenol, phenyl phenol, benzyl phenol, guajacol, butyl stilbene, (di) nitro phenol, nitro cresol, methyl salicylate, benzyl salicylate, mono-, di-, tri-, tetra- and penta-chlorophenol, chlorocresol, chloroxylenol, chlorothymol, p-chloro-o-cyclo-hexyl phenol, p-chloro-o-cyclopentyl phenol, p-chloro-o-n-hexyl phenol, p-chloro-o-benzyl phenol, p-chloro-o-benzyl-m-cresol and other phenols; β-naphthol, 8-hydroxy quinoline.

With respect to the metal (M), any metal having a valency of 2 or more may be used. Specific examples of suitable metals include Ca, Mg, Zn, Cu, Ba, Te, Pb, Fe, Co, Ni, Bi, Si, Ti, Mn, Al and Sn. Preferred examples are Co, Ni, Cu, Zn, Mn, and Te, in particular Cu and Zn. When synthesising the metal-containing co-polymer, the metal may be employed in the form of its oxide, hydroxide or chloride. The co-polymer to be used in the binder system in the coating composition according to the invention may be prepared as described in e.g. EP 0 471 204 B1, EP 0 342 276 B1 or EP 0 204 456 B1.

Monomers comprising the terminal groups of the general formula V above may be co-polymerised (in order to obtain the co-polymer) with other polymerisable unsaturated monomers, any customarily used ethylenically unsaturated monomer may be used. Examples of such monomers are methyl acrylate, methyl methacrylate, ethyl acrylate, ethyl methacrylate, propyl acrylate, propyl methacrylate, butyl acrylate, butyl methacrylate, octyl acrylate, octyl methacrylate, 2-ethyl hexyl acrylate, 2-ethyl hexyl methacrylate, methoxy ethyl methacrylate, styrene, vinyl toluene, vinyl pyridine, vinyl pyrolidone, vinyl acetate, acrylonitrile, methacrylo nitrile, dimethyl itaconate, dibutyl itaconate, di-2-ethyl hexyl itaconate, dimethyl maleate, di(2-ethyl hexyl) maleate, ethylene, propylene and vinyl chloride. One particular type of co-monomers is acrylic or methacrylic esters wherein the alcohol residue includes a bulky hydrocarbon radical or a soft segment, for example a branched alkyl ester having 4 or more carbon atoms or a cycloalkyl ester having 6 or more atoms, a polyalkylene glycol monoacrylate or monomethacrylate optionally having a terminal alkyl ether group or an adduct of 2-hydroxyethyl acrylate or methacrylate with caprolactone, e.g. as described in EP 0 779 304 A1.

If desired, hydroxy-containing monomers, such as 2-hydroxy ethyl acrylate, 2-hydroxy ethyl methacrylate, 2-hydroxy propyl acrylate, 2-hydroxy propyl methacrylate may also be used.

It should be noted that in the resulting co-polymer, not all the organic acid side groups need to contain a metal ester bond; some of the organic acid side groups may be left unreacted in the form of free acid, if desired.

The weight average molecular weight of the metal-containing co-polymer is generally in the range of from 1,000 to 150,000, such as in the range of from 3,000 to 100,000, preferably in the range of from 5,000 to 60,000.

In another interesting embodiment of the invention the coating composition further comprises an amount of an organic ligand at least equal to the ligand-to-metal co-ordination ratio of 1:1, said organic ligand being selected from the group consisting of aromatic nitro compounds, nitrites, urea compounds, alcohols, phenols, aldehydes, ketones, carboxylic acids and organic sulphur compounds, whereby the co-polymer defined above forms a polymer complex with the organic ligand in situ.

Examples of monobasic organic acids usable for forming the hybrid salt include monocarboxylic acids such as acetic, propionic, butyric, lauric, stearic, linolic, oleic, naphthenic, chloroacetic fluoroacetic, abietic, phenoxyacetic, valeric, dichlorophenoxyacetic, benzoic or napthoic acid; and monosulphonic acids such as benzenesulphonic acid, p-toluenesulphonic acid, dodecylbenzenesulphonic acid, naphthalenesulphonic or p-phenylbenzenesulforic acid.

A preferred method for producing the polymeric hybrid salt has been disclosed in Japanese Patent Kokai No. 16809/1989.

Further Binder Components

The above-mentioned binder systems (e.g. the non-aqueous dispersion binder system and the silylated acrylate binder system) may have included therein—as a part of the binder system—one or more further binder components. It should be understood that the binder components mentioned below may also constituted the binder system, cf. the general presentation of the binder system.

Examples of such further binder components are: rosin, rosin derivatives such as metal salts of rosin i.e. resinates, oils such as linseed oil and derivatives thereof, castor oil and derivatives thereof, soy bean oil and derivatives thereof; and other polymeric binder components such as saturated polyester resins; polyvinylacetate, polyvinylbutyrate, polyvinylchloride-acetate, copolymers of vinyl acetate and vinyl isobutyl ether; vinylchloride; copolymers of vinyl chloride and vinyl isobutyl ether; alkyd resins or modified alkyd resins; hydrocarbon resins such as petroleum fraction condensates; chlorinated polyolefines such as chlorinated rubber, chlorinated polyethylene, chlorinated polypropylene; styrene copolymers such as styrene/butadiene copolymers, styrene/methacrylate and styrene/acrylate copolymers; acrylic resins such as homopolymers and copolymers of methyl methacrylate, ethyl methacrylate, n-butyl methacrylate, isobutyl methacrylate and isobutyl methacrylate; hydroxy-acrylate copolymers; polyamide resins such as polyamide based on dimerised fatty acids, such as dimerised tall oil fatty acids; cyclised rubbers; epoxy esters; epoxy urethanes; polyurethanes; epoxy polymers; hydroxy-polyether resins; polyamine resins; etc., as well as copolymers thereof.

The terms "rosin", "resinate" and the like is intended to refer to gum rosin; wood rosin of grades B, C, D, E, F, FF, G, H, I,3, K, L, M, N, W-G, W-W (as defined by the ASTM 0509 standard); virgin rosin; hard rosin; yellow dip rosin; NF wood rosin; tall oil rosin; or colophony or colophonium. The terms "rosin" and "resinate" and the like are also intended to include suitable types of modified rosin, in particular oligomerisation; hydrogenation; dehydrogenation hydrogenation/disproportionation/dismutation; etc., that will reduce the amount of conjugated non-aromatic double bonds.

It should be understood that the group of further binder components may include polymeric flexibilisers such as those generally and specifically defined in WO 97/44401 that is hereby incorporated by reference.

The dry matter of such further binder components is typically 0-10% by wet weight.

Further Constituents of the Binder Phase

The binder phase (i.e. the phase corresponding to the continuous phase of the final (dry) paint coat) may—besides the binder system (including the further binder components)—of course also include dyes, additives and solvents, as well as other suitable constituents to be included in the binder phase of coating compositions.

Examples of dyes are 1,4-bis(butylamino)anthraquinone and other anthraquinone derivatives; toluidine dyes etc.

Examples of additives are plasticizers such as chlorinated paraffin; phthalates such as dibutyl phthalate, benzylbutyl phthalate, dioctyl phthalate, diisononyl phthalate and diisodecyl phthalate; phosphate esters such as tricresyl phosphate, nonylphenol phosphate, octyloxipoly(ethyleneoxy)ethyl phosphate, tributoxyethyl phosphate, isooctylphosphate and 2-ethylhexyl diphenyl phosphate; sulfonamides such as N-ethyl-p-toluensulfonamide, alkyl-p-toluene sulfonamide; adipates such as bis(2-ethylhexyl)adipate), diisobutyl adipate and di-octyladipate; phosphoric acid triethyl ester; butyl stearate; sorbitan trifoliate; and epoxidised soybean oil; surfactants such as derivatives of propylene oxide or ethylene oxide such as alkylphenol-ethylene oxide condensates; ethoxylated monoethanolamides of unsaturated fatty acids such as ethoxylated monoethanolamides of linoleic acid; sodium dodecyl sulfate; alkylphenol ethoxylates; and soya lecithin; wetting agents and dispersants; defoaming agents such as silicone oils; stabilisers such as stabilisers against light and heat, e.g. hindered amine light stabilisers (HALS), 2-hydroxy-4-methoxybenzophenone, 2-(5-chloro-(2H)-benzotriazol-2-yl)-4-methyl-6-(tert-butyl)phenol, and 2,4-ditertbutyl-6-(5-chlorobenzotriazol-2-yl)phenol; stabilisers against moisture or water scavengers, substituted isocyanates, substituted silanes and ortho formic acid triethyl ester; stabilisers against oxidation such as butylated hydroxyanisole; butylated hydroxytoluene; propylgallate; tocopherols; 2,5-di-tert-butyl-hydroquinone; L-ascorbyl palmitate; carotenes; vitamin A; inhibitors against corrosion such as aminocarboxylates, ammonium benzoate, barium/-calcium/zinc/ magnesium salts of alkylnaphthalene sulfonic acids, zinc phosphate; zinc metaborate; coalescing agents such as glycols, 2-butoxy ethanol, and 2,2,4-trimethyl-1,3-pentanediol monoisobutyrate; and thickeners and anti-settling agents such as aluminiumtristearate, aluminiummonostearate, ricinus oil, xanthan gum, salicylic acid, hydrogenated castor oil, polyamide waxes and polyethylene waxes. Dehydrating agents such as orthopropionic acid ester, orthoformic acid ester, orthoacetic acid ester, alkoxysilane, alkyl silicates like tetra ethyl ortosilicate, or isocyanates.

It is preferred that the coating compositions comprise dyes and additives in a cumulative amount of 0-20%, e.g. 1-20%, by solids volume of the coating composition.

When related to the total weight of the coating composition, it is preferred that the coating compositions comprise dyes and additives in a cumulative amount of 0-10%, e.g. 1-10%, by wet weight of the coating composition.

Examples of solvents are alcohols such as methanol, ethanol, propanol, isopropanol, butanol, isobutanol and benzyl alcohol; aliphatic, cycloaliphatic and aromatic hydrocarbons such as white spirit, cyclohexane, toluene, xylene and naphtha solvent; ketones such as methyl ethyl ketone, acetone, methyl isobutyl ketone, methyl isoamyl ketone, diacetone alcohol and cyclohexanone; ether alcohols such as 2-butoxyethanol, propylene glycol monomethyl ether, ethylene glycol monoethyl ether, ethyl ether and butyl diglycol; esters such as ethyl acetate, propyl acetate, methoxypropyl acetate, n-butyl acetate and 2-ethoxyethyl acetate; chlorinated hydrocarbons such as methylene chloride, tetrachloroethane and trichloroethylene; and mixtures thereof.

When related to the total weight of the coating composition, it is preferred that the coating compositions comprise one or more solvents in a cumulative amount of 0-60%, e.g. 10-60%, by wet weight of the coating composition.

In the present context the term "% by wet weight" is intended to mean the weight/weight percentage of the wet matter of the coating composition. It should be understood that solvents are included.

In the present context the term "% by solids volume" is intended to mean the volume/volume percentage of the solid (i.e. non-volatile) matter of the coating composition. It should be understood that any solvents (i.e. volatiles) are disregarded.

Preferred Embodiments

Currently preferred embodiments of the present invention are the following coating compositions:

A. An enzyme-based self-polishing coating composition comprising 50-75% by solids volume of a binder phase in the form of a binder system and 25-50% by solids volume of a pigment phase, said pigment phase comprising (i) starch and (ii) an enzyme selected from amylases in an amount of 20-49% by solids volume of the dry coating, and said enzyme being immobilised on said starch.

B. An enzyme-based self-polishing coating composition comprising 50-75% by solids volume of a binder phase in the form of a binder system and 25-50% by solids volume of a pigment phase, said pigment phase comprising (i) starch and (ii) an enzyme selected from amylases in an amount of 1-10% by solids volume of the dry coating, and said enzyme being immobilized on said starch.

C. An enzyme-based self-polishing coating composition comprising 50-75% by solids volume of a binder phase in the form of a binder system and 25-50% by solids volume of a pigment phase, said pigment phase comprising (i) starch and (ii) an enzyme selected from amylases in an amount of 1-10% by solids volume of the dry coating, and said enzyme being immobilized on said starch and an amount of 10-41% by solids volume of one or more pigments selected from a group consisting of cuprous oxide and zinc oxide.

D. An enzyme-based self-polishing coating composition comprising 50-75% by solids volume of a binder phase in the form of a binder system and 25-50% by solids volume of a pigment phase, said pigment phase comprising (i) starch and (ii) an enzyme selected from amylases in an amount of 20-49% by solids volume of the dry coating, and said enzyme being immobilised on said starch, and antifouling agent in an amount of 0.05-20% by solids volume of the dry coating.

E. An enzyme-based self-polishing coating composition comprising 50-75% by solids volume of a binder phase in the form of a binder system and 25-50% by solids volume of a pigment phase, said pigment phase comprising (i) starch and (ii) an enzyme selected from amylases in an amount of 20-49% by solids volume of the dry coating, and said enzyme being immobilised on said starch, and an antifouling agent in an amount of 0.05-20% by solids volume of the dry coating, said antifouling agent chosen from a the group consisting of pyridine-triphenylborane, 2-(p-chlorophenyl)-3-cyano-4-bromo-5-trifluoromethylpyrrole and imidazole containing compounds, such as Medetomidine.

F. An enzyme-based self-polishing coating composition comprising 50-75% by solids volume of a binder phase in the form of a binder system and 25-50% by solids volume of a pigment phase, said pigment phase comprising (i) starch and (ii) an enzyme selected from amylases in an amount of 1-10% by solids volume of the dry coating, and said enzyme being immobilized on said starch, and an antifouling agent in an amount of 1-20° A) by solids volume of the dry coating.

G. An enzyme-based self-polishing coating composition comprising 50-75% by solids volume of a binder phase in the form of a binder system and 25-50% by solids volume of a pigment phase, said pigment phase comprising (i) starch and (ii) an enzyme selected from amylases in an amount of 1-10% by solids volume of the dry coating, and said enzyme being immobilized on said starch, and an antifouling agent in an amount of 0.05-20% by solids volume of the dry coating, said antifouling agent chosen from the group consisting of pyridine-triphenylborane, 2-(p-chlorophenyl)-3-cyano-4-bromo-5-trifluoromethyl pyrrole and imidazole containing compounds, such as Medetomidine.

Preparation of the Coating Composition

The present invention also provides a method for the preparation of an enzyme-based self-polishing coating composition as defined in any one of claims 1-9, said method comprising the step of bringing (i) a polysaccharide and (ii) an enzyme capable of facilitating hydrolysis of said polysaccharide, wherein said enzyme is immobilized on a carrier material, in admixture with a binder system and one or more constituents selected from dyes, additives, solvents, pigments, fillers, fibres and anti-fouling agents, and any other suitable constituents to be included in either the binder phase or the pigment phase of coating compositions.

The coating composition of the present invention is prepared usually by mixing and dispersing the above components all at once or in a divided fashion by a conventional apparatus for producing coating composition (paints), such as a ball mill, a pearl mill, a three-roll mill, a high speed disperser. The coating compositions according to the invention, optionally containing fibres, may be filtrated using bag filters, patron filters, wire gap filters, wedge wire filters, metal edge filters, EGLM turnoclean filters (ex Cuno), DELTA strain filters (ex Cuno), and Jenag Strainer filters (ex Jenag), or by vibration filtration. The coating composition of the present invention thus prepared may be coated as it is or after having the viscosity adjusted by a diluting solvent, on a ship or a maritime structure having a rust preventive coating material coated thereon, by e.g. airless spray-coating, air spray-coating, roller coating or brush coating. The exact technique chosen depends upon the object to be protected and also upon the particular composition (such as its viscosity etc.) and upon the particular situation. Preferred applications techniques are spraying and by means of a brush or a roller.

Preferably the immobilised enzymes and their substrates are added to the coating composition as powders, and in a preferred embodiment of the invention, immobilisation of the polysaccharide-degrading enzyme is done by spray-drying from a water-based slurry of the enzyme and the carrier material.

Depending on the application technique, it is desirable that the coating composition comprises solvent(s) so that the solids volume ratio (SVR) is in the range of 30-100%, such as 30-70%.

The invention further relates to a marine structure coated with one or several layers, in particular successive layers, of a coating composition as defined hereinabove.

The coating composition according to the invention may be applied to a marine structure to be protected in one or several successive layers, typically 1 to 5 layers, preferably 1 to 3 layers. The dry film thickness (DFT) of the coating applied per layer will typically be 10 to 300 µm, preferably 20 to 250 µm, such as 40 to 200 µm. Thus, the total dry film thickness of the coating will typically be 10 to 900 µm, preferably 20 to 750 µm, in particular 40 to 600 µm, such as 80 to 400 µm.

The marine structure to which the coating composition according to the invention may be applied to may be any of a wide variety of solid objects that come into contact with water, for example vessels (including but not limited to boats, yachts, motorboats, motor launches, ocean liners, tugboats, tankers, container ships and other cargo ships, submarines (both nuclear and conventional), and naval vessels of all types); pipes; shore and off-shore machinery, constructions and objects of all types such as piers, pilings, bridge substructures, floatation devices, underwater oil well structures etc; nets and other mariculture installations; cooling plants; and buoys; and is especially applicable to the hulls of ships and boats and to pipes.

Prior to the application of a coating composition to a marine structure, the marine structure may first be coated with a primer-system which may comprise several layers and may be any of the conventional primer systems used in connection with application of coating compositions to marine structures. Thus, the primer system may include an anti-corrosive primer optionally followed by a layer of an adhesion-promoting primer.

The above-mentioned primer system may, for example, be a combination of an epoxy resin having an epoxy equivalent of from 160 to 600 with its curing agent (such as an amino type, a carboxylic acid type or an acid anhydride type), a combination of a polyol resin with a polyisocyanate type curing agent, or a coating material containing a vinyl ester resin, an unsaturated polyester resin or the like, as a binder system, and, if required, further containing a thermoplastic resin (such as chlorinated rubber, an acrylic resin or a vinyl chloride resin), a curing accelerator, a rust preventive pigment, a colouring pigment, an extender pigment, a solvent, a trialkoxysilane compound, a plasticizer, an additive (such as an antisagging agent or a precipitation preventive agent), or a tar epoxy resin type coating material, as a typical example.

Use and Method

The present invention further provides the use of a polysaccharide and an enzyme capable of facilitating hydrolysis of said polysaccharide, said enzyme being immobilized on a carrier material, in a coating composition to provide self-polishing of said coating composition. In particular, the enzyme is immobilised on said polysaccharide.

The present invention further provides a method for providing a self-polishing effect of a coating composition, the method comprising the step of incorporating into the coating composition a polysaccharide and an enzyme capable of facilitating hydrolysis of said polysaccharide, said enzyme being immobilized on a carrier material. In particular, the enzyme is immobilised on said polysaccharide.

The specifications above, including the specifications regarding the polysaccharide and the enzyme, also apply in connection with the use and the method described above.

In one preferred embodiment of the above-specified use and the above-specified method, respectively, the enzyme is glucoamylase and the polysaccharide is starch. In a particular variant, the glucoamylase is immobilized on the starch, e.g. by spray-drying.

EXAMPLES

Test for Water Soluble Content of Polysaccharides

The water-soluble content of polysaccharides is determined gravimetrically. The polysaccharide is mixed in deionised water and stirred effectively. The slurry is then centrifuged at 15,000 rpm in ten minutes, and the dry matter content of the supernatant is determined gravimetrically.

Polishing Rate Test

Polishing and leaching characteristics are measured using a rotary set-up similar to the one described by Kiil et al. (Kiil, S, Weinell, C E, Yebra, D M, Dam-Johansen, K, "*Marine biofouling protection: design of controlled release antifouling paints.*" In: Ng, K M, Gani, R, Dam-Johansen, K (eds.) Chemical Product Design; Towards a Perspective Through Case Studies, 231 DBN-13: 978-0-444-52217-7. Part II (7), Elsevier. (2006)). The set-up consists of a rotary rig, which has two concentric cylinders with the inner cylinder (rotor, diameter of 0.3 m and height 0.17 m) capable of rotation. The cylinder pair is immersed in a tank containing about 400-500 liters of Artificial Seawater (cf. Table 1).

TABLE 1

| Composition of Artificial Seawater | |
| --- | --- |
| Salt | Concentration in g/L |
| NaCl | 32 |
| $MgSO_4 \cdot 7H_2O$ | 14 |
| $NaHCO_3$ | 0.2 |

The tank is fitted with baffles to break the liquid flow, which enhances turbulence and enables faster mixing of the species released from the paints and enhance heat transfer from a thermostating system. The purpose of using two cylinders is to create a close approximation to couette flow (flow between two parallel walls, where one wall moves at a constant velocity). The rotor is operated at 20 knots at 25° C. (unless otherwise specified), and the pH is adjusted frequently to 8.2 using 1 M sodium hydroxide or 1 M hydrochloric acid.

Samples are prepared using overhead transparencies (3M PP2410) that are primed using two-component paint (Hempadur 4518 ex Hempel's Marine Paints A/S) applied using a Doctor Blade applicator with a gap size of 200 μm. Coating samples are applied adjacent to each other using a Doctor Blade applicator with a gap of 250 μm. After drying for 1 day, the coated transparency is cut in strips of 2 cm resulting in eight samples of 1.5×2 cm² on a long (21 cm) strip. The strips are mounted on the rotor, and left to dry for a week.

After one week, the test is initiated, and during the experiment, samples are removed after 35, 65 and 140 days in order to inspect the polishing and leaching depths. The samples are dried for three days at ambient conditions, after which they are cut in half and cast in paraffin. The internal front of the sample is planed off before total film thickness and leached layer thickness is established using light microscopy (coating cross-section inspection).

Antifouling Property Test

An acrylic test panel (15×20 cm²), sandblasted on one side to facilitate adhesion of the coating, is first coated with 80 μm (DFT) of a commercial vinyl tar primer (Hempanyl 16280 ex Hempel's Marine Paints A/S) applied by air spraying. After a minimum drying time of 24 hours in the laboratory at room temperature the test paint is applied with a Doctor Blade type applicator, with four gap sizes with a film width of 80 mm. One coat was applied in a DFT of 90-100 μm. After at least 72 hours drying the test panels are fixed on a rack and immersed in sea water.

In this test site the panels are immersed in seawater with salinity in the range of 29-31 parts per thousand at a temperature in the range of 29-31° C. Every 4-12 weeks, inspection of the panels is made and the antifouling performance is evaluated according to the scale shown in Table 2. One score is given for each of the fouling types: algae and animals.

TABLE 2

| Scale for grading the performance of coatings undergoing static antifouling testing | |
| --- | --- |
| Score | Fouled area (%) |
| 0 | 0% fouling |
| 1 | 0-2% fouling |
| 2 | 3-5% fouling |
| 3 | 6-25% fouling |
| 4 | 26-50% fouling |
| 5 | 51-100% fouling |

The fouling species of most relevance are animals. For animal fouling a level of 1 is considered good. For algal fouling, a level of up to grade 2 is acceptable.

Test for Residual Enzymatic Activity after Prolonged Exposure to Sea-Water

Paint film pieces from the rotor trial were immersed in Artificial Seawater (cf. Table 1) in 6-well ELISA plastic plates and analysed for glucose development through 3 days of incubation at 20-25° C. Gentle movement of the solvent was applied with a shaker board (IKA KS130 control) operated continuously at 100 rpm. The glucose concentration in the solvent phase was analysed by a standard glucose assay (see below). The activity was the calculated as SGU-P (Starch-Glucoamylase Unit in Paint) where 1 SGU-P is defined as the surface area required for releasing 1 mg glucose per hour.

Glucose Assay: The glucose sample (10 μl) was mixed with a substrate blend (290 μl) with excess HOX (hexose oxidase), Horseradish Peroxidase and ABTS (2,2'-azino bis(3-ethylbenzothiazoline-6-sulfonic acid). Fully HOX-degradadion of glucose produces glucolactone and H2O2, which reacts (oxidises) ABTS and induces a spectrometric detectable colorimetric response correlating to the sample glucose concentration. The glucose concentration was quantified by measuring the absorption at 405 nm and by using a standard curve of 0 to 0.4 mg ID-Glucose/ml. The substrate blend used was comprised by: 4.6 ml 100 mM K2HPO4-pH 6.3; 200 μl ABTS solution (500 mg ABTS Sigma A-1888 to 100 ml H2O); 200 μl Peroxidase solution (10 mg Sigma P-6782 to 100 ml 100 mM K2HPO4-pH 6.3); and 200 μl purified HOX (HOX from *Chondrus crispus* was used as fermentation broth prepared as described in patent application EP-A-0832245 and purified according to Rand et al (T. Rand, K. B. Qvist, C. P. Walter & C. H. Poulsen, FEBS Journal, 2006, 273, 2693-2703).

Preparation of Spray-Dried Starch with Glucoamylase (Laboratory Scale)

Corn starch, obtained as C*gel 03401 from Cargill, and glucoamylase obtained from Danisco A/S are spray-dried from a water-based slurry. 75 g starch and glucoamylase in a concentration of 56 units/g slurry are spray-dried from a water volume of 500 mL. Air inlet temperature is kept at 135° C., and the air and powder outlet temperature is 80° C. At the spray nozzles, water cooling with 0° C. water is used. The apparatus is a Mini Spray Dryer B-191 from Buchi laboratory equipment.

Preparation of Spray-Dried Starch with Glucoamylase (Pilot Scale)

Corn starch, obtained as C*gel 03401 from Cargill, and glucoamylase obtained from Danisco A/S was mixed in water to form slurry comprised by 7.5 kg starch, 15 kg water, and glucoamylase at a concentration of 3325 mU/g starch (unless otherwise specified) and spray-dried. The activity was as measured on the pure enzyme preparation before addition to the starch slurry. Spray-drying was performed in a Niro NP 6.3 spray unit with an atomizer wheel operated at 15000 rpm and a feed rate of 40-50 kg slurry/h. Drying air inlet and outlet temperatures were 190-200° C. and 95-110° C., respectively. The air flow was 480-520 m$^3$/h.

Test for Enzyme Activity of Glycoamylase Immobilised to Starch

Activity of the spray-dried starch-glucoamylase powder was determined to be 10-15 SGU/g. 1 SGU (Starch-Glucoamylase Unit) corresponds to the amount of starch-glucoamylase powder releasing 1 mg glucose per hour at 25° C. and pH 4.5 in a 2 w/w % starch-glucoamylase dispersion, calculated as an average glucose release through the initial 1-3 hours of incubation). Glucose developed was isolated with the supernatant by centrifugation and analysed with a standard glucose assay using a glucose standard curve for quantification.

Composition of Test Paints

TABLE 3

Test paints based on a silylated acrylic binder system with or without starch with glucoamylase

| | Comparative ref. paint 1 | | Model paint 1 | | Model paint 2 | | Model Paint 3 | |
|---|---|---|---|---|---|---|---|---|
| | % wet weight | % solids volume | % wet weight | % solids volume | % wet weight | % solids volume | % wet weight | % solids volume |
| Binder phase | | | | | | | | |
| Binder system comprised silylated acrylic copolymer solution and rosin | 28 | 52 | 28 | 52 | 29 | 52 | 32 | 52 |
| Additives | 4 | 8 | 4 | 8 | 4 | 8 | 4 | 8 |
| Xylene, Xylen, Kemetyl Denmark | 8 | 0 | 8 | 0 | 9 | 0 | 9 | 0 |
| Pigment phase | | | | | | | | |
| Calcium magnesium aluminium silicate, Rockfibre Roxul 1000 MS603, Brenntag Denmark | 1 | 1 | 1 | 1 | 1 | 1 | 1 | 1 |
| Fumed silica, Aerosil 200, Degussa Germany | 1 | 2 | 1 | 2 | 1 | 2 | 1 | 2 |
| Micronized Natural Red Iron Oxide, OSO NR 839M, Tor Minerals International US | 5 | 4 | 5 | 4 | 6 | 4 | 6 | 4 |
| Starch with glucoamylase[#] | 0 | 0 | 0.5 | 1.00 | 2.4 | 5.00 | 5 | 10.00 |
| Copper pyrithione, Copper Omadine Powder, Arch UK Biocides UK (antifouling agent) | 3 | 6 | 3 | 6 | 4 | 6 | 4 | 6 |
| Copper (I) oxide, Red Copp 97N, Chemet US | 50.00 | 28 | 49 | 27 | 44 | 23 | 37 | 18 |
| Total | 100 | 101 | 99.5 | 101 | 100.4 | 100 | 99.2 | 100 |
| Total Pigment phase | | 40 | | 40 | | 40 | | 40 |

[#]As prepared in pilot scale.

TABLE 4

Test paints based on a silylated acrylic binder system and common antifouling coating fillers

|  | Comparative reference paint 2 | | Comparative reference paint 3 | |
|---|---|---|---|---|
|  | % wet weight | % solids volume | % wet weight | % solids volume |
| Binder phase | | | | |
| Binder system comprised of silylated acrylic copolymer solution and rosin | 29 | 52 | 31 | 52 |
| Additives | 4 | 8 | 4 | 8 |
| Xylene, Xylen, Kemetyl Denmark | 8 | 0 | 9 | 0 |
| Pigment phase | | | | |
| Calcium magnesium aluminium silicate, Rockfibre Roxul 1000 MS603, Brenntag Denmark | 1 | 1 | 1 | 1 |
| Fumed silica, Aerosil 200, Degussa Germany | 1 | 2 | 1 | 2 |
| Micronized Natural Red Iron Oxide, OSO NR 839M, Tor Minerals International US | 5 | 4 | 6 | 4 |
| Feldspar, Minex S-10, North Cape Minerals Norway | 4 | 5 | 9 | 10 |
| Copper pyrithione, Copper Omadine Powder, Arch UK Biocides UK (antifouling agent) | 4 | 6 | 4 | 6 |
| Copper (I) oxide, Red Copp 97N, Chemet US | 43 | 23 | 36 | 18 |
| Total | 99 | 101 | 101 | 101 |
| Total Pigment phase | | 40 | | 40 |

TABLE 5

Test paints based on a NAD binder system with or without starch with glucoamylase

|  | Comparative reference paint 4 | | Model paint 4 | | Model paint 5 | |
|---|---|---|---|---|---|---|
|  | % wet weight | % solids volume | % wet weight | % solids volume | % wet weight | % solids volume |
| Binder phase | | | | | | |
| Binder system comprised of NAD acrylic resin copolymer, RSAN-V-SPD#-55, DAI Nippon Japan; polyvinyl methyl ether and rosin | 19 | 50 | 19 | 50 | 20 | 50 |
| Additives | 3 | 5 | 3 | 5 | 3 | 5 |
| Xylene, Xylen, Kemetyl Denmark | 18 | 0 | 18 | 0 | 18 | 0 |
| 3,3-Dimethylbutanone, Methylisobutylketon, Kemetyl Denmark | 1 | 0 | 1 | 0 | 1 | 0 |
| Pigment phase | | | | | | |
| Calcium magnesium aluminium silicate, Rockfibre Roxul 1000 MS603, Brenntag Denmark | 4 | 5 | 4 | 5 | 4 | 5 |
| Organic derivative of a special magnesium montmorillonite, Bentone 38, Elementis Specialites Belgium | 1 | 2 | 1 | 2 | 1 | 2 |
| Fumed silica, Aerosil 200, Degussa Germany | 0.3 | 0.5 | 0.3 | 0.5 | 0.3 | 0.5 |
| Micronized Natural Red Iron Oxide, OSO NR 839M, Tor Minerals International US | 4 | 3 | 4 | 3 | 4 | 3 |
| Zinc oxide, Larvik Zinx Oxide, Umicore Norway | 8 | 5 | 8 | 5 | 8 | 5 |
| Starch with glucoamylase[#] | 0 | 0 | 0.4 | 1 | 1.3 | 3 |
| Copper pyrithione, Copper Omadine Powder, Arch UK Biocides UK (antifouling agent) | 4 | 7 | 4 | 7 | 4 | 7 |
| Copper(I) oxide, Lolo Tint 97, Chemet US | 39 | 23 | 38 | 22 | 35 | 20 |
| Total | 101.3 | 100.5 | 100.7 | 100.5 | 99.6 | 100.5 |
| Total Pigment phase | | 45 | | 45 | | 45 |

[#]As prepared in pilot scale

TABLE 6

Test paints based on a NAD binder system and respectively starch with glucoamylase or common antifouling coating fillers

|  | Model paint 6 | | Model paint 7 | | Comparative reference paint 5 | | Comparative reference paint 6 | |
|---|---|---|---|---|---|---|---|---|
|  | % wet weight | % solids volume | % wet weight | % solids volume | % wet weight | % solids volume | % wet weight | % solids volume |
| Binder phase | | | | | | | | |
| Binder system: NAD acrylic resin copolymer, RSAN-V-SPD#-55, DAI Nippon Japan; polyvinyl methyl ether and rosin | 20 | 50 | 22 | 50 | 20 | 50 | 21 | 50 |
| Additives | 3 | 4 | 3 | 4 | 3 | 4 | 3 | 4 |
| Xylene, Xylen, Kemetyl Denmark | 19 | 0 | 20 | 0 | 18 | 0 | 19 | 0 |
| Methylisobutylketon, Kemetyl Denmark | 1 | 0 | 1 | 0 | 1 | 0 | 1 | 0 |
| Pigment phase | | | | | | | | |
| Calcium magnesium aluminium silicate, Rockfibre Roxul 1000 MS603, Brenntag Denmark | 4 | 5 | 5 | 5 | 4 | 5 | 4 | 5 |
| Organic derivative of a special magnesium montmorillonite, Bentone 38, Elementis Specialites Belgium | 1 | 2 | 1 | 2 | 1 | 2 | 1 | 2 |
| Fumed silica, Aerosil 200, Degussa Germany | 0.3 | 0.5 | 0.3 | 0.5 | 0.3 | 0.5 | 0.3 | 0.5 |
| Micronized Natural Red Iron Oxide, OSO NR 839M, Tor Minerals International US | 4 | 3 | 4 | 3 | 4 | 3 | 4 | 3 |
| Zinc oxide, Larvik Zinx Oxide, Umicore Norway | 1 | 1 | 2 | 1 | 2 | 1 | 2 | 1 |
| Starch with glucoamylase[#] | 2 | 5 | 5 | 10 | | | | |
| Feldspar, Minex S-10, North Cape Minerals Norway | | | | | 4 | 5 | 8 | 10 |
| Copper pyrithione, Copper Omadine Powder, Arch UK Biocides UK (antifouling agent) | 4 | 7 | 4 | 7 | 4 | 7 | 4 | 7 |
| Copper(I) oxide, Lolo Tint 97, Chemet US | 40 | 22 | 33 | 17 | 39 | 22 | 32 | 17 |
| Total | 99.3 | 99.5 | 100.3 | 99.5 | 101.3 | 99.5 | 99.3 | 99.5 |
| Total Pigment Phase | | 46 | | 46 | | 46 | | 46 |

[#]As prepared in pilot scale

TABLE 7

Test paints based on a binder system especially suited for yachts

|  | Comparative reference paint 7 | | Model paint 8 | |
|---|---|---|---|---|
|  | % wet weight | % solids volume | % wet weight | % solids volume |
| Binder phase | | | | |
| fully hydrogenated rosin, Foral (TM) AX-E, Eastman chemical company US | 19 | 36 | 19 | 36 |
| polyvinyl methyl ether, Lutonal M 40, BASF Germany | 10 | 9 | 10 | 9 |
| acryllic copolymer, Synocryl 874 N 40, Cray Valley US | 16 | 12 | 16 | 12 |
| Additives | 1 | 2 | 1 | 2 |
| Xylene, Xylen, Kemetyl Denmark | 10 | | 10 | |
| Pigment phase | | | | |
| Calcium magnesium aluminium silicate, Rockfibre Roxul 1000 MS603, Brenntag Denmark | 7 | 5 | 7 | 5 |
| Zeolite, Purmol powder 4ST, Zeochem Switzerland | 1 | 1 | 1 | 1 |
| Micronized Natural Red Iron Oxide, OSO NR 839M, Tor Minerals International US | 11 | 5 | 11 | 5 |
| Zinc oxide, Larvik Zinx Oxide, Umicore Norway | 3 | 1 | 3 | 1 |
| Starch with glucoamylase[#] | | | 24 | 30 |
| Starch (without enzyme) | 24 | 30 | | |
| Total | 101 | 99 | 101 | 99 |
| Total Pigment Phase | | 41 | | 41 |

[#]As prepared in pilot scale

TABLE 8

Test paints based on a NAD binder system with starch with or without glucoamylase.

|  | Model paint 7 | |
|---|---|---|
|  | % wet weight | % solids volume |
| Binder phase | | |
| Binder system comprised of NAD acrylic resin copolymer, RSAN-V-SPD#-55, DAI Nippon Japan; polyvinyl methyl ether and rosin | 22 | 50 |
| Additives | 3 | 4 |
| Xylene, Kemetyl Denmark | 20 | 0 |
| Methylisobutylketon, Kemetyl Denmark | 1 | 0 |

TABLE 8-continued

Test paints based on a NAD binder system with starch with or without glucoamylase.

|  | Model paint 7 | |
|---|---|---|
|  | % wet weight | % solids volume |
| Pigment phase | | |
| Calcium magnesium aluminium silicate, Rockfibre Roxul 1000 MS603, Brenntag Denmark | 5 | 5 |
| Organic derivative of a special magnesium montmorillonite, Bentone 38, Elementis Specialites Belgium | 1 | 2 |
| Fumed silica, Aerosil 200, Degussa Germany | 0.3 | 0.5 |
| Micronized Natural Red Iron Oxide, OSO NR 839M, Tor Minerals International US | 4 | 3 |
| Zinc oxide, Larvik Zinx Oxide, Umicore Norway | 2 | 1 |
| Starch with glucoamylase (see Table 9) | 5 | 10 |
| Copper pyrithione, Copper Omadine Powder, Arch UK Biocides UK (antifouling agent) | 4 | 7 |
| Copper(I) oxide, Lolo Tint 97, Chemet US | 33 | 17 |
| Total | 100.3 | 99.5 |
| Total Pigment Phase | | 46 |

TABLE 9

Test paints with different activity of glucoamylase in spray-dried starch with glucoamylase (composition as in Table 8)

|  | Activity before spray-drying |  |
|---|---|---|
| Spray-dried starch with glucoamylase | 478 mU/g starch | Model Paint 9 |
| Spray-dried starch with glucoamylase | 4,290 mU/g starch | Model Paint 10 |
| Spray-dried starch with glucoamylase | 50,000 mU/g starch | Model Paint 11 |

[#]As prepared in pilot scale; samples with various activities were obtained by adding variable amounts of enzyme per mass starch.

The coatings were produced on two-speed Dial 37-33v mixer. The ingredients are mixed and ground to a fineness of <30 μm. Any ingredients sensitive to the high shear forces and temperature in the grinding process may are added in the let-down.

Example 1

Characterisation of Various Starch Qualities as Coating Ingredients

The starches presented in Table 10 were tested for the amount of water-soluble contaminants in the experiment described above. The results are presented in Table 11.

TABLE 10

Source, name and suppliers of starches tested

| Name | Commercial name | Source | Supplier | Gelatinisation (° C.) | Average equivalent spherical volume diameter (μm) |
|---|---|---|---|---|---|
| R1 | Remy FG | Rice | Remy | 65-73 | 2-8 |
| R2 | Remy B7 | Rice | Remy | 72 | 5 |
| R3 | Remygel 663 | Rice | Remy | 57 | 5 |
| R4 | Remy DR | Rice | Remy | 77 | 5 |
| R5 | Remyline AX DR | Waxy rice | Remy | 65-73 | 5 |
| C1 | C*gel 03401 | Corn | Cargill | 62-71 | 15 |

TABLE 10-continued

Source, name and suppliers of starches tested

| Name | Commercial name | Source | Supplier | Gelatinisation (° C.) | Average equivalent spherical volume diameter (μm) |
|---|---|---|---|---|---|
| C2 | Clearam MH 0500 | Corn | Roquette | 62-71 | 15 |
| C3 | Clearam MH 10 15 | Corn | Roquette | 62-71 | 15 |
| C4 | Clearam CI 30 00 | Waxy corn | Roquette | 62-71 | 15 |
| C5 | Clearam CI 10 00 | Waxy corn | Roquette | 62-71 | 15 |
| C6 | Clearam CH 15 05 | Waxy corn | Roquette | 62-71 | 15 |
| C7 | HI-CAT 21370 | Waxy corn | Roquette | 62-71 | 15 |
| T1 | Clearam TJ 2015 | Tapioca | Roquette | 59-70 | 20 |

Whereas normal starch contains about ¾ of the highly branched amylopectin, waxy starch is 100% amylopectin. Gelatinisation temperatures in Table 10 refer to the temperature at which the starches form a gel.

TABLE 11

The amount of water soluble contaminants in the starch types presented in Table 10.

|  | Wt % water soluble material |
|---|---|
| R1 | 2.7 |
| R2 | 0.83 |
| R3 | 5 |
| R4 | 1.44 |
| R5 | 1.6 |
| C1 | 0.12 |
| C2 | 0.15 |
| C3 | 0.677 |
| C4 | 0.28 |
| C5 | 0.23 |
| C6 | 0.205 |
| C7 | 2.93 |
| T1 | 0.13 |

In Table 11 it is seen that the starch-type containing the least amount of water soluble material is the Corn starch type, C*gel 03401 from Cargill ("C1"). This type of starch has therefore been preferred for the subsequent examples.

Example 2

Polishing Rate and Leached Layer Depth of Test Paints Based on a Silylated Acrylic Binder with or without Starch with Glucoamylase The test paints based on the silylated acrylic binder system (see Tables 3 and 4) were used in polishing rate testing. Table 12 shows the results of the polishing rate and the leached layer depth for the coatings. The leached layer thicknesses after 140 days are provided as a measure of the steady-state leached layer thickness.

TABLE 12

Polishing rate and leached layer depth

| Test paint | Polishing rate (μm/10,000 Nautical miles) | Leached layer in % of comparative reference paint 1 |
|---|---|---|
| Comparative reference paint 1 | 2.7 | 100 |
| Model paint 1 | 5.3 | 106 |
| Model paint 2 | 3.5* | — |
| Model paint 3 | 3.5 | 115 |
| Comparative reference paint 2 | 3.5 | 100 |
| Comparative reference paint 3 | 4 | 136 |

*Polishing rate after 65 days.

The example shows that a powder consisting of glucoamylase immobilised on starch can be used as substitute for cuprous oxide in coating compositions based on silylated acrylic binder systems without lowering polishing rate. Compared to feldspat (Comparative reference paint 3), the polishing is somewhat similar, however, the leached layer is thicker in the comparative reference paint than in the model paints. This means that the diffusion resistance of the antifouling active ingredients is increased, and therefore antifouling effect is compromised.

Example 3

Comparison of the Antifouling Performance of Test Paints Based on a Silylated Acrylic Binder with or without Starch with Glucoamylase The test paints based on a silylated acrylic binder system (see Tables 3 and 4) were tested in the antifouling property test in Singapore. After 8 weeks immersion, the panels were inspected. The grades from the inspection are seen in Table 13.

TABLE 13

Grades from inspection of test paints after 8 weeks of antifouling property testing in Singapore

| | Blank panel | Comparative reference paint 1 | Model paint 1 | Model paint 2 | Model paint 3 | Comparative reference paint 2 | Comparative reference paint 3 |
|---|---|---|---|---|---|---|---|
| Algae | 4 | 1 | 1 | 1 | 1 | 2 | 1 |
| Animals | 3 | 2 | 1 | 1 | 3 | 2 | 3 |

The table shows that the antifouling properties of the coatings containing glucoamylase immobilised on starch are not compromised (Model paints 1 and 2). Comparing to the coatings containing feldspat as filler (Comparative reference paints 2 and 3), it is seen that the antifouling effect of the coatings based on glucoamylase immobilised on starch is better.

Example 4

Polishing Rate and Leached Layer Depth of Test Paints Based on a NAD Binder System with or without Starch with Glucoamylase The test paints based on the NAD binder system (see Tables 5 and 6) were subjected to the polishing rate test. The results are shown in Table 14. The leached layer thicknesses after 140 days are provided as a measure of the steady-state leached layer thickness.

TABLE 14

Polishing rate and leached layer depth

| Model paint | Polishing rate (µm/10,000 Nautical miles) | Leached layer in % of comparative reference paint 4 |
|---|---|---|
| Comparative reference paint 4 | 5.0 | 100 |
| Model paint 4 | 7.2 | 98 |

TABLE 14-continued

Polishing rate and leached layer depth

| Model paint | Polishing rate (µm/10,000 Nautical miles) | Leached layer in % of comparative reference paint 4 |
|---|---|---|
| Model paint 5 | 3.3 | 74 |
| Model paint 6 | 8.4 | 81 |
| Model paint 7 | 5.0 | 90 |
| Comparative reference 5 | 4.4 | 97 |
| Comparative reference 6 | 1.7 | 132 |

It is seen that the novel coating ingredient can be added (Model paints 4, 6 and 7) without compromising polishing and leaching behaviour. Furthermore, it is seen that using glucoamylase immobilised on starch as filler (Model paints 5, 6 and 7) generally lowers the leached layer thickness compared to the reference coatings (Comparative reference paints 5 and 6).

Example 5

Comparison of the Antifouling Performance of Test Paints Based on a NAD Binder System with or without Starch with Glucoamylase The test paints based on a NAD binder system (see Tables 5 and 6) were tested in the antifouling property test. After 8 weeks immersion the panels were inspected. The grades from the inspection are provided in Table 15.

TABLE 15

Grades from inspection of test paints paints after 8 weeks of antifouling property testing in Singapore

| | Blank panel | Comp. ref. paint 4 | Model paint 4 | Model paint 5 | Model paint 6 | Model paint 7 | Comp. ref. Paint 5 | Comp. ref. paint 6 |
|---|---|---|---|---|---|---|---|---|
| Algae | 4 | 1 | 2 | 1 | 2 | 2 | 1 | 1 |
| Animals | 3 | 1 | 1 | 0 | 1 | 1 | 1 | 2 |

The table shows that the antifouling properties of the coatings containing glucoamylase immobilised on starch are not compromised (Model paints 4-7). An algal fouling level up to grade 2 is acceptable.

Example 6

Polishing Rate of Test Paints Based Entirely on Starch with Glucoamylase as Water Soluble Part of the Pigment Phase Comparative reference paint 7 and Model paint 8 (see Table 7) were subjected to polishing rate testing. The results are provided in Table 16.

TABLE 16

| Model paint # | Polishing rate |
|---|---|
| | Polishing rate (μm per 10,000 Nautical miles) |
| Comparative reference paint 7 | 0 |
| Model paint 8 | 5.6 |

The results show that it is possible to achieve polishing of a yacht-based antifouling coating, when it contains glucoamylase immobilised on starch as the only active pigment (Model paint 8). In comparison, a coating containing starch without immobilised glucoamylase does not polish (Comparative reference 7).

Example 7

Comparison of the Antifouling Performance of Test Paints Based on a NAD Binder System Based Coating Composition with or without Starch with Glucoamylase The test paints based on the NAD binder system (see Tables 8 and 9) were subjected to the polishing rate test. The results are shown in Table 17. The leached layer thicknesses after 35 days at a temperature of 25° C. are provided as a measure of the steady-state leached layer thickness. Residual enzyme activity was measured after 21 days.

It is seen that there is a tendency that the polishing increases with increased enzyme activity. Furthermore it is seen that the residual enzyme activity increases with increasing enzyme activity prior to spray drying.

The invention claimed is:

1. An enzyme-based self-polishing coating composition comprising:
   a binder phase in the form of a binder system; and
   a pigment phase, wherein said pigment phase comprising comprises (i) a polysaccharide and (ii) an enzyme capable of facilitating hydrolysis of said polysaccharide, wherein said enzyme is immobilized on said polysaccharide, and wherein said polysaccharide is starch, and said enzyme is selected from α-amylase, β-amylase, and glucoamylase.

2. The coating composition according to claim 1, wherein said starch constitutes 1-30% solids by volume of said coating composition.

3. The coating composition according to claim 1, wherein said starch constitutes 1-40% solids by volume of said coating composition.

4. The coating composition according to claim 1, wherein said the ratio between said enzyme and said polysaccharide is 0.05-200,000 milliunits enzyme(s) per g polysaccharide.

5. The coating composition according to claim 1, wherein the binder phase constitutes 30-80% solids by volume of the coating composition and the pigment phase constitutes 20-70% solids by volume of the coating composition.

6. The coating composition according to claim 1, wherein said coating composition further comprises 0.05-20% solids by volume of one or more antifouling agents.

7. A marine structure coated with one or several layers of a coating composition as defined in claim 1.

8. A method for the preparation of an enzyme-based self-polishing coating composition as defined in claim 1, said method comprising: the steps of
   (a) providing an enzyme immobilized on a polysaccharide, wherein the enzyme is capable of facilitating hydrolysis of said polysaccharide, wherein said polysaccharide is starch, and said enzyme is selected from α-amylase, β-amylase, and glucoamylase, and

TABLE 17

| | Polishing rate, leached layer depth and residual enzyme activity | | |
|---|---|---|---|
| Model paint # | Polishing rate (μm/10,000 Nautical miles) The decrease in film thickness between inspection after 21 and 35 days is used to calculate the polishing rate. | Leached layer in % of comparative reference paint 9 | Residual enzyme activity Activity (mg glucose/m2/h) |
| Model Paint 9 | 9.5 | 100 | 0.123 |
| Model Paint 10 | — | — | 0.315 |
| Model Paint 11 | 15.2 | 103 | 0.364 |

(b) bringing said enzyme immobilized on said polysaccharide in admixture with a binder system and one or more constituents selected from dyes, additives, solvents, pigments, fillers, fibres and anti-fouling agents so as to form said coating composition.

9. A method for providing a self-polishing effect of a coating composition, the method comprising the step of coating a marine structure with one or more layers of the coating composition according to claim 1, thereby providing said self-polishing effect.

* * * * *